United States Patent [19]

Burri et al.

[11] Patent Number: 5,270,313
[45] Date of Patent: Dec. 14, 1993

[54] SULFONAMIDES AND USES

[75] Inventors: Kaspar Burri, Binningen, Switzerland; Martine Clozel, St. Louis, France; Walter Fischli, Allschwil, Switzerland; Georges Hirth, Huningue, France; Bernd M. Löffler, Oberrimsingen, Fed. Rep. of Germany; Henri Ramuz, Birsfelden, Switzerland

[73] Assignee: Hoffmann-La Roche Inc., Nutley, N.J.

[21] Appl. No.: 869,274

[22] Filed: Apr. 15, 1992

[30] Foreign Application Priority Data

Apr. 25, 1991 [CH] Switzerland .................. 1242/91
Feb. 6, 1992 [CH] Switzerland .................. 343/92

[51] Int. Cl.$^5$ ............... C07D 239/69; A61K 31/505
[52] U.S. Cl. .................. 514/252; 544/327; 544/319; 544/295; 544/296; 544/238; 544/309; 544/311; 544/317
[58] Field of Search .............. 544/327, 319, 295, 309; 514/256, 269, 252

*Primary Examiner*—John M. Ford
*Attorney, Agent, or Firm*—George M. Gould; George W. Johnston; William Krovatin

[57] ABSTRACT

Sulfonamides of formula I, in which the symbols $R^1$-$R^6$, X, Y and n have the significance given in the description and which are in part novel compounds, and salts thereof, which can be used as active ingredients for the manufacture of medicaments for the treatment of circulatory disorders, especially hypertension, ischemia, vasospasms and angina pectoris, are described.

25 Claims, No Drawings

SULFONAMIDES AND USES

BRIEF SUMMARY OF THE INVENTION

The invention relates to the use of sulfonamides as medicaments and to sulfonamide compounds. More particularly, the invention relates to the use of compounds of the formula

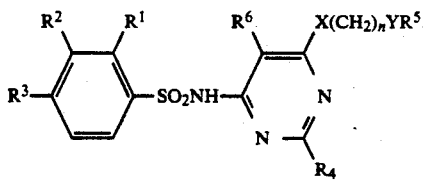

wherein $R^1$ is hydrogen, lower-alkyl, lower-alkoxy, lower-alkylthio, halogen or trifluoromethyl;

$R^2$ is hydrogen, halogen, lower-alkoxy, hydroxy-lower-alkoxy or trifluoromethyl; and $R^3$ is hydrogen lower-alkyl, hydroxy, halogen, alkylthio, cycloalkyl, hydroxy-lower-alkyl, hydroxy-lower-alkoxy, hydroximino-lower-alkyl, lower-alkenyl, oxo-lower-alkyl, trifluoromethyl, trifluoromethoxy, lower-alkoxy, lower-alkoxy-lower-alkoxy or aryl-lower-alkoxy; or $R^2$ and $R^3$ taken together are butadienyl;

$R^4$ is hydrogen, lower-alkyl, aryl or heteroaryl;

$R^5$ is hydrogen, lower-alkanoyl, benzoyl, heterocyclylcarbonyl or tetrahydropyran-2-yl;

$R^6$ is a residue of the formula

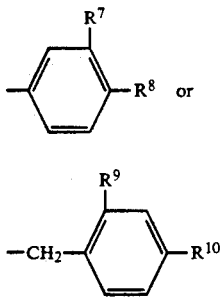

$R^7$ is hydrogen, lower-alkoxy or nitro; and $R^8$ is hydrogen, halogen, lower-alkyl, lower-alkoxy, lower-alkylthio, nitro, hydroxy, amino or trifluoromethyl; or $R^7$ and $R^8$ taken together are butadienyl;

$R^9$ is hydrogen, halogen, lower-alkyl, lower-alkoxy, lower-alkylthio or trifluoromethyl;

$R^{10}$ is hydrogen, halogen, lower-alkyl, lower-alkoxy or lower-alkylthio;

X and Y each, independently, is O, S or NH; and n is 2, 3 or 4;

and pharmaceutically acceptable salts thereof, for the treatment of circulatory disorders, particularly hypertension, ischemia, vasospasms and angina pectoris.

In another aspect, the invention relates to compounds of formula I, wherein $R^6$ is

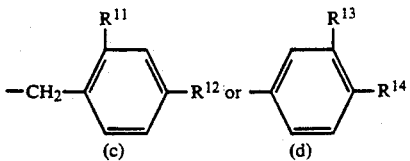

and wherein $R^{11}$ is halogen, lower-alkoxy, lower-alkylthio or trifluoromethyl, $R^{12}$ is hydrogen or lower-alkoxy, $R^{13}$ is hydrogen, lower-alkoxy or nitro, $R^{14}$ is hydrogen, halogen, lower-alkyl, lower alkoxy, lower-alkylthio or nitro, or $R^{13}$ and $R^{14}$ taken together are butadienyl.

DETAILED DESCRIPTION OF THE INVENTION

The invention relates to the use of sulfonamides as medicaments and to sulfonamide compounds. More particularly, the invention relates to the use of compounds of the formula

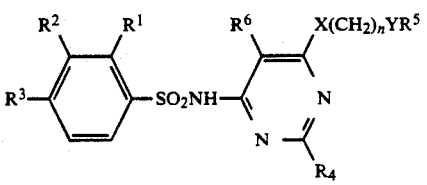

wherein $R^1$ is hydrogen, lower-alkyl, lower-alkoxy, lower-alkylthio, halogen or trifluoromethyl;

$R^2$ is hydrogen, halogen, lower-alkoxy, hydroxy-lower-alkoxy or trifluoromethyl; and $R^3$ is hydrogen lower-alkyl, hydroxy, halogen, alkylthio, cycloalkyl, hydroxy-lower-alkyl, hydroxy-lower-alkoxy, hydroximino-lower-alkyl, lower-alkenyl, oxo-lower-alkyl, trifluoromethyl, trifluoromethoxy, lower-alkoxy, lower-alkoxy-lower-alkoxy or aryl-lower-alkoxy; or $R^2$ and $R^3$ taken together are butadienyl;

$R^4$ is hydrogen, lower-alkyl, aryl or heteroaryl;

$R^5$ is hydrogen, lower-alkanoyl, benzoyl, heterocyclylcarbonyl or tetrahydropyran-2-yl;

$R^6$ is a residue of the formula

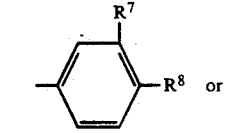

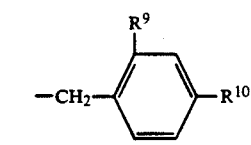

$R^7$ is hydrogen, lower-alkoxy or nitro; and $R^8$ is hydrogen, halogen, lower-alkyl, lower-alkoxy, lower-alkylthio, nitro, hydroxy, amino or trifluoromethyl; or $R^7$ and $R^8$ taken together are butadienyl;

$R^9$ is hydrogen, halogen, lower-alkyl, lower-alkoxy, lower-alkylthio or trifluoromethyl;

$R^{10}$ is hydrogen, halogen, lower-alkyl, lower-alkoxy or lower-alkylthio;

X and Y each, independently, is O, S or NH; and n is 2, 3 or 4;

and pharmaceutically acceptable salts thereof, for the treatment of circulatory disorders, particularly hypertension, ischemia, vasospasms and angina pectoris.

In another aspect, the invention relates to compounds of formula I, wherein $R^6$ is

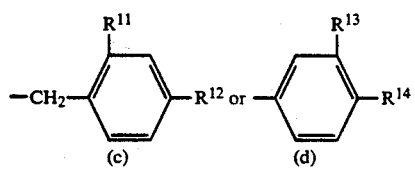

and wherein $R^{11}$ is halogen, lower-alkoxy, lower-alkylthio or trifluoromethyl, $R^{12}$ is hydrogen or lower-alkoxy, $R^{13}$ is hydrogen, lower-alkoxy or nitro, $R^{14}$ is hydrogen, halogen, lower-alkyl, lower alkoxy, lower-alkylthio or nitro, or $R^{13}$ and $R^{14}$ taken together are butadienyl.

The term "lower", as used herein, denotes saturated groups with 1-7 C atoms, preferably 1-4 C atoms, and unsaturated groups with 2-7 C atoms, preferably 2-4 C atoms. Alkyl, alkoxy, alkylthio and alkenyl groups as well as alkyl groups as components of alkanoyl groups can be straight-chain or branched. Methyl, ethyl, propyl, isopropyl, butyl, sec. and tert.butyl are examples of such alkyl groups. Vinyl and allyl are examples of alkenyl groups. Aryl-lower-alkoxy is, for example, benzyloxy. Halogen denotes fluorine, chlorine, bromine and iodine; chlorine is preferred. Examples of aryl residues are phenyl and substituted phenyl residues, with halogen, alkyl and alkoxy especially coming into consideration as substituents. Examples of heteroaryl residues are especially monocyclic 5- and 6-membered heteroaromatic residues having nitrogen or sulfur as the hetero atom, such as, pyrimidinyl, pyridyl, pyrazinyl, pyridazinyl and thienyl. Heterocyclyl-carbonyl residues are, e.g., 2-, 3- or 4-pyridylcarbonyl; 3-methylisoxazol-5-yl-carbonyl; 2- or 3-furoyl; and 2-or 3-thenoyl.

Sulfonamides which fall under formula I of the invention, and which are other than the compounds of formula I wherein $R^6$ is

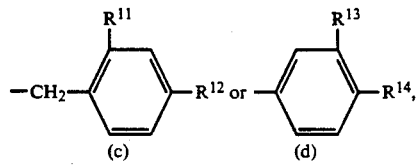

are known from Patent Publication DE 1 545 944. The referred-to known sulfonamides have blood pressure lowering activity. It has now been surprisingly found that the compounds of formula I are inhibitors of endothelin receptors. The compounds of formula I can therefore be used for the treatment of illnesses associated with endothelin activities, particularly, circulatory disorders, such as, hypertension, ischemia, vasospasms and angina pectoris.

A preferred group of compounds of formula I comprises those wherein $R^6$ is a residue of the formula

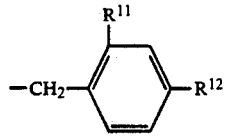

and wherein $R^{11}$ is halogen, lower-alkoxy, lower-alkylthio or trifluoromethyl; and $R^{12}$ is hydrogen or lower-alkoxy and $R^1$-$R^5$, X, Y and n have the significance given above.

A further preferred group of compounds of formula I comprises those wherein $R^6$ is a residue of the formula

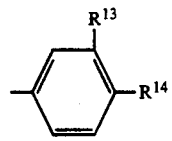

and wherein $R^{13}$ is hydrogen, lower-alkoxy or nitro; $R^{14}$ is hydrogen, halogen, lower-alkyl, lower-alkoxy, lower-alkylthio or nitro; or $R^{13}$ and $R^{14}$ taken together are butadienyl; and $R^1$-$R^5$, X, Y and n have the significance given above.

The compounds of formula I can be prepared by reacting a compound of the formula

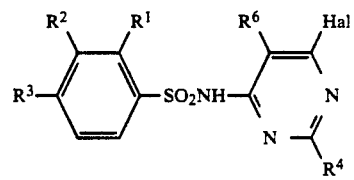

wherein $R^1$, $R^2$, $R^3$, $R^4$ and $R^6$ have the significance given above and Hal is halogen, with a compound of the formula

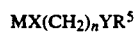

$$MX(CH_2)_nYR^5 \quad \text{III}$$

wherein X, Y, n and $R^5$ have the significance given above and M is an alkali metal, and, if desired, modifying substituents present in the resulting compound of formula I and/or converting the compound of formula I obtained into a salt.

In a preferred embodiment of the process, a compound of formula II wherein $R^6$ is the residue (c) or (d), described above, is used as the starting material.

The reaction of a compound of formula II with a compound of formula III is conveniently carried out using the glycol from which the compound III is derived, for example, ethylene glycol, when n is 2. The alkali metal M is preferably sodium. The reaction is conveniently carried out with heating, for example, to 70°-120° C. In a preferred embodiment, the monosodium salt of ethylene glycol, propylene glycol or butylene glycol is used as the compound of formula III.

Substituents which are present in the thus-obtained compound of formula I can be modified. For example, $R^5$ as a hydroxy group can be esterified or etherified. A nitro group can be reduced to the amino group. $R^3$ as lower-alkenyl group can be oxidized to the carbonyl group or to an alkanone group, for example, using $OsO_4$ or $NaIO_4$. The thus-formed carbonyl group can be reduced to the hydroxy group, for example, using sodium borohydride, or can be converted into a corresponding tertiary alcohol with an alkyl-Grignard compound or can be converted into the oxime with hydroxylamine. These conversions can be carried out in a known manner whereby $R^5$ a hydroxy group $R^5$ is first transformed into an ether group, for example, the tetrahydropyranyl ether, or an ester group, for example, the acetate. If desired, these groups can again be cleaved in a known manner alternatively a transformation of $R^5$ as a hydroxy group by esterification or etherification can also be carried out without subsequent transformation of other reactive groups in the molecule. The compounds of formula I can be converted into salts, for example, alkali salts, such as sodium (Na) and potassium (K) salts, in a known manner.

The compounds of formulas II and III, which are used as starting materials, insofar as they are not known or their preparation is not described hereinafter, can be prepared in analogy to known methods or to methods described hereinafter.

The compounds of formula II can be prepared in accordance with the following Reaction Scheme:

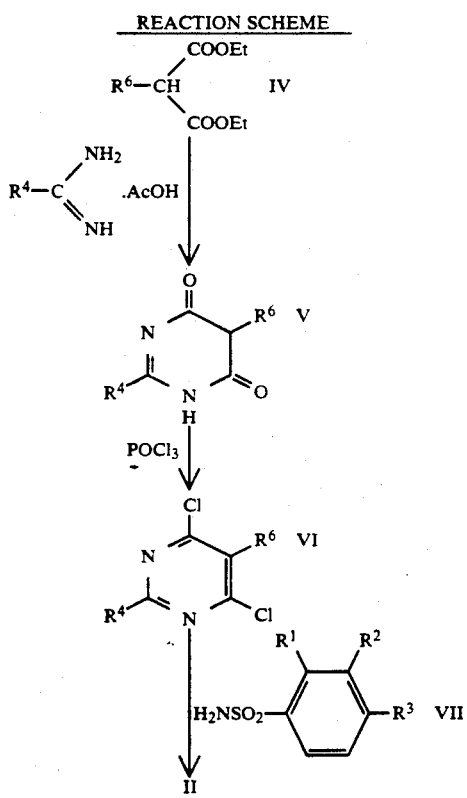

wherein $R^1$, $R^2$, $R^3$, $R^4$ and $R^6$ have the significance given above.

Condensation of a compound of formula IV with formamidine acetate or a homologous compound, such as, acetamidine acetate or acetamidine hydrochloride yields the corresponding pyrimidinedione of formula V. With phosphorus oxychloride, there is obtained therefrom the dichloro compound of formula VI which yields the corresponding compound of formula II upon reaction with a compound of formula VII. All of these reactions are standard operations and can be carried out under conditions which are usual for such reactions and which are familiar to a person skilled in the art. Compounds of formula IV in which $R^6$ is a residue (a) can be obtained from corresponding phenylacetic acid esters of the formula $R^6CH_2COOE_t$ by reaction with diethyl carbonate in the presence of sodium ethylate. Compounds of formula IV in which $R^6$ is a residue (b) can be prepared by Knoevenagel condensation of diethyl malonate with a corresponding aldehyde $R^6CHO$ and subsequent hydrogenation of the condensation product.

Salts of the compounds of formula I, which have a basic functionality, that is, the pyrimidine moiety, are prepared by the reaction of an appropriate Compound of formula I with a non-toxic pharmaceutically acceptable acid. In general, the referred to compounds of formula I form pharmaceutically acceptable addition salts with, for example, both pharmaceutically acceptable organic and inorganic acids, such as, acetic acid, succinic acid, formic acid, methanesulfonic acid, p-toluenesulfonic acid, hydrochloric acid, nitric acid, phosphoric acid, sulfuric acid and the like.

The inhibitory activity of the compounds of formula I on endothelin receptors can be demonstrated using the test procedures described hereinafter:

I. Inhibition of endothelin binding to human placenta membranes (see Life Sci 44:1429 (1989)

Human placenta is homogenized in 5 mM Tris buffer, pH 7.4, which contains 1 mM $MgCl_2$ and 250 mM sucrose. The product of the homogenization is centrifuged at 4° C. for 15 minutes at 3000 g. The supernatant containing the plasma membrane fractions is centrifuged for 30 minutes at 72000 g and the precipitate obtained from, in each case, 10 g of original tissue is suspended in 1 ml of 75 mM Tris buffer, pH 7.4, containing 25 mM $MgCl_2$ and 250 mM sucrose and freeze-dried at $-20°$ C. in 1 ml aliquots.

For the binding assay, the freeze-dried membrane preparations are thawed and, after centrifugation at 20° C. for 10 minutes at 25000 g, re-suspended in assay buffer (50 mM Tris buffer, pH 7.4, containing 25 mM $MnCl_2$, 1 mM EDTA and 0.5% bovine serum albumin). 100 µl of this membrane suspension, containing 70 µg of protein, are incubated with 50 µl of $^{125}$I-endothelin (specific activity 2200 Ci/mMol) in assay buffer (25000 cpm, final concentration 20 pM) and 100 µl of assay buffer which contains varying concentrations of the test compound. The incubation is carried out at 20° C. for 2 hours or at 4° C. for 24 hours. The separation of free and membrane-bound radioligands is carried out by filtration over a glass fiber filter.

The inhibitory activity of compounds of formula I determined in this test procedure is given in Table 1 as the $IC_{50}$, that is, as the concentration [µM] which is required to inhibit the specific binding of $^{125}$I-endothelin by 50%.

TABLE 1

| Compound of Example | $IC_{50}$ [µM] |
|---|---|
| 1 | 5 |
| 54 | 3 |
| 63 | 1.6 |
| 64 | 2 |
| 66 | 0.5 |
| 83 | 0.7 |
| 84 | 1 |

II. Inhibition of endothelin-induced contractions in isolated aorta rings of the rat Rings with a thickness of 5 mm were dissected from the thorax aorta of adult Wistar-Kyoto rats. The endothelium was removed by rubbing the internal surface slightly. Each ring was immersed in an isolated bath at 37° C. in 10 ml of Krebs-Henseleit solution while gassing with 95% $O_2$ and 5% $CO_2$. The isometric tension of the rings was measured. The rings were stretched to an initial tension of 3 g. After incubation with the test compound or vehicle for 10 minutes cumulative doses of endothelin-1 were added. The activity of the test compound was determined by calculating the dosage ratio, that is, the correcting shift (shift to higher values) of the $EC_{50}$ of endothelin induced by 100 μm of test compound, whereby $EC_{50}$ denotes the endothelin concentration required for a half-maximum contraction. The greater this dosage ratio is, then the more potent is the inhibition of the test compound of the biological activity of endothelin-1. The $EC_{50}$ of endothelin in the absence of test compounds is 0.3 nM.

The values for the correcting shift of the $EC_{50}$ of endothelin thus-obtained with compounds of I are given in Table 2.

TABLE 2

| Compound of Example | Dosage ratio (correcting shift) |
|---|---|
| 1 | 30 |
| 54 | 21 |
| 63 | 23 |
| 64 | 19 |
| 66 | 96 |
| 83 | 86 |
| 84 | 106 |

III. The inhibitory activity of the compounds of formula I on vasoconstriction can be observed in vivo in the rat in the test procedure described hereinafter:

Rats were anaesthetized with Na thiobutabarbital (100 mg/kg i.p.). A catheter was placed through the femoral artery in order to measure the systemic arterial blood pressure and a catheter was placed in the inferior vena cava via the femoral vein for the injection of the test compounds. A Doppler probe was placed around the left renal artery and attached to a Doppler measuring device. A renal ischemia was produced by pinching off the left renal artery at its point of emergence for 45 minutes. The test compounds were administered 10 minutes prior to the onset of the ischemia intra-arterially (i.a.) in doses of 5 mg/kg or intraveneously (i.v) in doses of 10 mg/kg. In control experiments, the renal blood flow was reduced by 43±4% in comparison to the pre-ischemic value.

The results obtained with two compounds of formula I are given in Table 3.

TABLE 3

| Compound of Example | % Decrease in the renal of blood flow |
|---|---|
| 1 i.a. | 7 |
| 83 i.v. | 29 |

In view of the capability of inhibiting endothelin binding, the compounds of formula I can be used as agents for the treatment of illnesses which are associated with processes which increase vasoconstriction. Examples of such illnesses are high blood pressure, coronary diseases, cardiac insufficiency, renal and myocardial ischemia, renal insufficiency, dialysis, cerebral ischemia, cardiac infarct, migraine, subarachnoid haemorrhage, Raynaud syndrome and pulmonary high blood pressure. They can also be used in atherosclerosis, the prevention of restenosis after balloon-induced vessel dilation, inflammations, gastric and duodenal ulcers, ulcus cruris, gram-negative sepsis, shock, glomerulonephritis, renal cholic, glaucoma, asthma, in the theraphy and prophylaxis of diabetic complications and complications with the administration of cyclosporin as well as other illnesses which are associated with endothelin activities.

The compounds of formula I can be administered orally, rectally, parenterally, for example, intravenously, intramuscularly, subcutaneously, intrathecally or transdermally; or sublingually or as ophthalmological preparations, or as aerosols. Examples of such pharmaceutical forms are capsules, tablets, suspensions or solutions for oral administration, suppositories, injection solutions, eye drops, salves or spray solutions.

Intravenous, intramuscular or oral administration is a preferred form of use. The dosage at which the compounds of formula I are administered in effective amounts depends on the nature of the specific active ingredient, the age and the requirements of the patient and the mode of administration. In general, doses of about 0.1–100 mg/kg body weight per day come into consideration. The pharmaceutical compositions or preparations containing the compounds of formula I can contain inert as well as pharmacodynamically active additives. Tablets or granulates, for example, can contain a series of binders, fillers, carriers or diluents. Liquid preparations can be present, for example, in the form of a sterile water-miscible solutions. Capsules can contain a filler or thickener in addition to the active ingredient. Furthermore, flavor improving additives as well as substances usually used as preserving, stabilizing, moisture-retaining and emulsifying agents as well as salts for varying the osmotic pressure, buffers and other additives can be present.

The previously mentioned carriers and diluents can comprise organic or inorganic substances, for example, water, gelatin, lactose, starch, magnesium stearate, talc, gum arabic, polyalkylene glycols and the like. It is a prerequisite that all adjuvants used in the preparation of the pharmaceutical composition are non-toxic.

The Examples which follow further illustrate the invention. All temperatures are given in degrees centigrade, unless otherwise stated.

EXAMPLE 1

A solution of 0.046 g of Na in 1.5 ml of absolute ethylene glycol was treated with 0.216 g of N-[6-chloro-5-(p-chloro-phenyl)-4-pyrimidinyl]-α,α,α-trifluoro-p-toluenesulfonamide with the exclusion of moisture and heated at 100° C. for 3 hours, thereafter cooled to room temperature and treated with 2.3 ml of 1N HCl. The mixture was taken up in ethyl acetate, the organic extracts were washed with water, dried and evaporated under reduced pressure. The precipitate remaining behind was recrystallized from $CH_2Cl_2$, isopropyl ether and n-hexane and yielded N-[5-(p-chlorophenyl)-6-(2-hydroxyethoxy)-4-pyrimidinyl]-α,α,α-trifluoro-p-toluenesulfonamide, melting point 160°–162° C.

The starting material was prepared as follows:

A solution of 1.052 g of α,α,α-trifluorobenzenesulfon-amide potassium and 0.520 g of 4,6-dichloro-5-(p-chlorophenyl)pyrimidine (Chem. Abstr. 63, 18078-$HO_4$) in 6 ml of abs. DMF was heated at 100° C. for 4 hours. Thereafter, it was cooled to room temperature and treated with 5 ml of 1N HCl. The mixture was taken up in ethyl acetate. The organic extracts were washed with water, dried and evaporated under reduced pressure. There was obtained N-[6-chloro-5-(p-chlorophenyl)-4-pyrimidinyl]-α,α,α-trifluoro-p-toluenesulfonamide as a white substance of melting point 275° C. (from acetonitrile).

EXAMPLE 2

In analogy in Example 1, from N-[6-chloro-5-(p-chlorophenyl)-4-pyrimidinyl]-p-(trifluoromethoxy)benzenesulfonamide and ethylene glycol Na, there was obtained N-[5-(p-chlorophenyl)-6-(2-hydroxyethoxy)-4-pyrimidinyl]-p-(trifluoromethoxy)benzenesulfonamide, melting point 152° C. (from iso-propyl ether).

The starting material was obtained from 4,6-dichloro-5-(p-chlorophenyl)pyrimidine and p-(trifluoromethoxy)benzenesulfonamide potassium, melting point 240°–242° C.

EXAMPLE 3

In analogy to Example 1, from p-chloro-N-[6-chloro-5-(m-chlorophenyl)-4-pyrimidinyl]benzenesulfonamide and ethylene glycol Na, there was obtained p-chloro-N-[5-(m-chlorophenyl)-6-(2-hydroxyethoxy)-4-pyrimidinyl]benzenesulfonamide melting point 178°–180° C. (from acetone-isopropyl ether).

The starting material was prepared as follows:

a) 5.97 g of formamidine acetate were added to a solution of 3.96 g of Na and 100 ml of absolute methanol. After cooling, the solution to 10° C. 15.51 g of diethyl (m-chlorophenyl)malonate were added in portions. After 2.5 hours, the solvent was evaporated under reduced pressure. The residue was dissolved in water and the solution was adjusted to pH 5.0 with glacial acetic acid. The resulting precipitate was removed by filtration under suction, washed with water, ethanol and ether and dried at 70° C. under reduced pressure. There was obtained 5-(m-chlorophenyl)-4,6(1H,5H)-pyrimidinedione which was used directly in the next step.

b) A mixture of 10.6 g of 5-(m-chlorophenyl)-4,6(1H,5H)-pyrimidinedione, 36 ml of POCl$_3$ and 5.8 ml of N,N-dimethyl-aniline was boiled at reflux for 3 hours. After evaporation of the solvent under reduced pressure, the residue was treated with ice and the mixture was extracted with ether. The organic solvent was dried and evaporated under reduced pressure. The oily residue was taken up in n-hexane, whereby 4,6-dichloro-5-(m-chlorophenyl)-pyrimidine crystallized out. Melting point 93°–94° C.

c) From 4,6-dichloro-5-(m-chlorophenyl)-pyrimidine and p-chlorobenzenesulfonamide K, there was obtained p-chloro-N-[6-chloro-5-(m-chlorophenyl)-4-pyrimidinyl]benzenesulfonamide, melting point 226°–228° C. (from CH$_3$CN).

EXAMPLE 4

In analogy to Example 1, from p-chloro-N-[6-chloro-5-(p-fluorophenyl)-4-pyrimidinyl]benzenesulfonamide, there was obtained p-chloro-N-[5-(p-fluorophenyl)-6-(2-hydroxyethoxy)-4-pyrimidinyl]benzenesulfonamide, melting point 208°–212° C. (from CH$_3$CN).

The starting material was prepared as follows:

a) In analogy to Example 3, paragraph a), from diethyl (p-fluorophenyl)malonate and formamidine acetate, there was obtained 5-(p-fluorophenyl)-4,6(1H,5H)-pyrimidinedione as a solid which was used directly in the next step.

b) In analogy to Example 3, paragraph b) from 5-(p-fluorophenyl)-4,6(1H,5H)-pyrimidinedione and POCl$_3$, there was obtained 4,6-dichloro-5-(p-fluorophenyl)-pyrimidine, melting point 98°–99° C. (from n-hexane).

c) In analogy to Example 3, paragraph c), from 4,6-dichloro-5-(p-fluorophenyl)pyrimidine and p-chlorophenylsulfonamide K, there was obtained p-chloro-N-[6-chloro-5-(p-fluorophenyl)-4-pyrimidinyl]benzenesulfonamide, melting point 251°–254° C. (from methylene chloride-isopropyl ether).

EXAMPLE 5

In analogy to Example 1, from N-(6-chloro-5-(p-chlorophenyl)-4-pyrimidinyl]-p-fluorobenzenesulfonamide and ethylene glycol Na, there was obtained N-[5-(p-chlorophenyl)-6-(2-hydroxyethoxy)-4-pyrimidinyl]-p-fluorobenzenesulfonamide, melting point 181°–183° C. (from methylene chloride-isopropyl-ether).

The starting material was prepared from 4,6-dichloro-5-(p-chlorophenyl)pyrimidine and p-fluorophenylsulfonamide. Melting point 244°–246° C. (from methylene chloride-isopropyl ether).

EXAMPLE 6

In analogy to Example 1, from o-chloro-N-[6-chloro-5-(p-chlorophenyl)-4-pyrimidinyl]benzenesulfonamide and ethylene glycol Na, there was obtained o-chloro-N-[5-(p-chlorophenyl)-6-(2-hydroxyethoxy)-4-pyrimidinyl]benzenesulfonamide, melting point 183°–185° C. (from acetone and isopropyl ether).

The starting material was obtained from 4,6-dichloro-5-(p-chlorophenyl)pyrimidine and o-chlorophenylsulfonamide. Melting point 230°–234° C. (from CH$_3$CN).

EXAMPLE 7

In analogy to Example 1, from N-[6-chloro-5-(p-ethylphenyl)-4-pyrimidinyl]-p-cyclopentylbenzenesulfonamide and ethylene glycol Na, there was obtained p-cyclopentyl-N-[6-(2-hydroxyethoxy)-5-(p-ethylphenyl)-4-pyrimidinyl]benzenesulfonamide, melting point 145°–146° C. (from acetone and isopropyl ether).

The starting material was prepared from 4,6-dichloro-5-(p-ethylphenyl)pyrimidine and p-cyclopentylbenzenesulfon-amide, melting point 178°–180° C. (from acetonitrile and isopropyl ether).

EXAMPLE 8

In analogy to Example 1, from p-chloro-N-[6-chloro-5-(3,4-dimethoxyphenyl)-4-pyrimidinyl]benzenesulfonamide and ethylene glycol Na, there was obtained p-chloro-N-[5-(3,4-dimethoxyphenyl)-6-(2-hydroxyethoxy)-4-pyrimidinyl]benzene-sulfonamide, melting point 232°–234° C. (from CH$_3$CN).

The starting material was prepared as follows:

In analogy to Example 3, paragraph b), from 5-(3,4-dimethoxyphenyl)-4,6(1H,5H)-pyrimidinedione and POCl$_3$, there was prepared 4,6-dichloro-5-(3,4-dimethoxyphenyl)pyrimidine, melting point 151°–152° C. (from cyclohexane-ether), from which with p-chlorophenylsulfonamide, there was obtained p-chloro-N-[6-chloro-5-(3,4-dimethoxyphenyl)-4-pyrimidinyl]benzene-sulfonamide, melting point 201°–203° C. (from CH$_3$CN).

EXAMPLE 9

In analogy to Example 1, from 3,4-dichloro-N-[6-chloro-5-(p-chlorophenyl)pyrimidinyl]benzenesulfonamide and ethylene glycol Na, there is obtained 3,4- dichloro-N-[5-(p-chlorophenyl)-6-(2-hydroxyethoxy)-4-pyrimidinyl]benzenesulfonamide, melting point 181° C. (from CH₃CN and isopropyl ether).

EXAMPLE 10

In analogy to Example 1, from N-[6-chloro-5-(p-chlorophenyl)-4-pyrimidinyl]$\alpha,\alpha,\alpha,\alpha',\alpha',\alpha'$-hexafluoromethylxylenesulfonamide, there was obtained N-[5-(p-chlorophenyl)-6-(2-hydroxyethoxy)-4-pyrimidinyl]-$\alpha,\alpha,\alpha,\alpha',\alpha',\alpha'$-hexafluoro-3,5-xylenesulfonamide, melting point 156°–158° C. (from methylene chloride/n-hexane).

The starting material was prepared from 4,6-dichloro-5-(p-chlorophenyl)pyrimidine and 2,4-bis-trifluoromethyl-phenylsulfonamide. Melting point 132°–135° C. (from isopropyl ether); purity 92% (HPLC analysis).

EXAMPLE 11

In analogy to Example 1, from 3-chloro-N-[6-chloro-5-(p-chlorophenyl)-4-pyrimidinyl]-4-fluorobenzenesulfonamide and an excess of ethylene glycol Na, there was obtained 3-chloro-N-[5-(p-chlorophenyl)-6-(2-hydroxyethoxy)-4-pyrimidinyl]-4-(2-hydroxyethoxy)-benzenesulfonamide, melting point 138°–140° C. (from acetone-isopropyl ether).

The starting material was prepared from 4,6-dichloro-5-(p-chlorophenyl)pyrimidine and 3-chloro-4-fluorophenyl-sulfonamide. Melting point 239° C. (from methylene chloride-acetonitrile).

EXAMPLE 12

In analogy to Example 1, from p-chloro-N-[(6-chloro-5-(p-nitrophenyl)-4-pyrimidinyl]benzenesulfonamide and ethylene glycol Na, there was obtained p-chloro-N-[(6-(2-hydroxyethoxy)-5-(p-nitrophenyl)-4-pyrimidinyl]benzenesulfonamide, melting point 223°–225° C. (from methylene chloride-isopropyl ether).

The starting material was prepared from 4-chloro-5-(p-nitrophenyl)pyrimidine and p-chlorophenylsulfonamide; melting point 282°–285° C. (from CH₃CN).

EXAMPLE 13

In analogy to Example 1, from p-butoxy-N-[6-chloro-5-(p-chlorophenyl)-4-pyrimidinyl]benzenesulfonamide and ethylene glycol Na, there was obtained p-butoxy-N-[5-(p-chlorophenyl)-6-(2-hydroxyethoxy)-4-pyrimidinyl]benzenesulfonamide, melting point >300° C. (from isopropyl ether), purity 97.7% by HPLC analysis.

The starting material was prepared from 4,6-dichloro-5-(p-chlorophenyl)pyrimidine and 4-n-butoxyphenylsulfonamide. Melting point 234° C. (from CH₃CN).

EXAMPLE 14

In analogy to Example 1, from N-6-chloro-[5-(p-chlorophenyl)-4-pyrimidinyl]-3,4-dimethoxybenzenesulfonamide and ethylene glycol Na, there was obtained N-[5-(p-chlorophenyl)-6-(2-hydroxyethoxy)-4-pyrimidinyl]-3,4-dimethoxybenzene-sulfonamide, melting point 130°–132° C. (from isopropyl ether).

The starting material was prepared from 4,6-dichloro-5-(p-chlorophenyl)pyrimidine and 3,4-dimethoxyphenylsulfon-amide, Melting point 226° C. (from CH₃CN).

EXAMPLE 15

In analogy to Example 1, from o-chloro-N-[6-chloro-5-(p-chlorophenyl)-4-pyrimidinyl]-$\alpha,\alpha,\alpha$-trifluoro-p-toluene-sulfonamide and ethylene glycol Na, there was obtained 2-chloro-N-[5-(p-chlorophenyl)-6-(2-hydroxyethoxy)-4-pyrimidinyl]-$\alpha,\alpha,\alpha$-trifluoro-p-toluenesulfonamide, melting point 131° C. (from isopropyl ether).

The starting material was prepared from 4,6-dichloro-5-(p-chlorophenyl)pyrimidine and 2-chloro-$\alpha,\alpha,\alpha$-trifluoro-p-toluenesulfonamide; melting point 234° C. (from methylene chloride-acetonitrile).

EXAMPLE 16

In analogy to Example 1, from 6-chloro-N-[6-chloro-5-(p-chlorophenyl)-4-pyrimidinyl]-$\alpha,\alpha,\alpha$-trifluoro-m-toluene-sulfonamide and ethylene glycol Na, there was obtained 6-chloro-N-[5-(p-chlorophenyl)-6-(2-hydroxyethoxy)-4-pyrimidinyl]-$\alpha,\alpha,\alpha$-trifluoro-m-toluenesulfonamide, melting point 185°–186° C. (from isopropyl ether).

The starting material was prepared from 4,6-dichloro-5-(p-chlorophenyl)pyrimidine and $\alpha,\alpha,\alpha$-trifluoro-3-methyl-6-chlorophenylsulfonamide; melting point 232° C. (from isopropyl ether).

EXAMPLE 17

In analogy to Example 1, from 2,3,4-trichloro-N-[6-chloro-5-(p-chlorophenyl)-4-pyrimidinyl]benzenesulfonamide and ethylene glycol Na, there was obtained 2,3,4-trichloro-N-[(5-chlorophenyl)-6-(2-hydroxyethoxy)-4-pyrimidinyl]benzenesulfonamide, melting point 209°–211° C. (from methylene chloride-isopropyl ether).

The starting material was prepared from 4,6-dichloro-5-(p-chlorophenyl)pyrimidine and 2,3,4-trichlorophenylsulfon-amide; melting point 278°–280° C. (from CH₃CN).

EXAMPLE 18

In analogy to Example 1 from m-chloro-N-[6-chloro-5-(p-chlorophenyl)-4-pyrimidinyl]benzenesulfonamide and ethylene glycol Na, there was obtained m-chloro-N-[(p-chlorophenyl)-6-(2-hydroxyethoxy)-4-pyrimidinyl]benzenesulfonamide, melting point 179°–181° C. (from acetonitrile-isopropyl ether).

The starting material was prepared from 4,6-dichloro-5-(p-chlorophenyl)pyrimidine and 3-chlorophenylsulfonamide; melting point 219°–221° C. (from CH₃CN).

EXAMPLE 19

In analogy to Example 1, from 2,4-dichloro-N-[6-chloro-5-(p-chlorophenyl)-4-pyrimidinyl]benzenesulfonamide and ethylene glycol Na, there was obtained 2,4-dichloro-N-[5-(p-chlorophenyl)-6-(2-hydroxyethoxy)-4-pyrimidinyl]benzenesulfonamide, melting point 165°–167° C. (from CH₃CN).

The starting material was prepared from 4,6-dichloro-5-(p-chlorophenyl)pyrimidine and 2,4-dichlorophenylsulfonamide; melting point 252°–254° C. (from CH₃CN).

EXAMPLE 20

In analogy to Example 1, from N-[6-chloro-5-(p-chloro-phenyl)-4-pyrimidinyl]-$\alpha,\alpha,\alpha$-trifluoro-m-toluenesulfonamide and ethylene glycol Na, there was obtained N-[5-(p-chlorophenyl)-6-(2-hydroxyethoxy)-

4-pyrimidinyl]-α,α,α-trifluoro-m-toluenesulfonamide, melting point 148°–150° C. (from isopropyl ether).

The starting material was prepared from 4,6-dichloro-5-(p-chlorophenyl)pyrimidine and α,α,α-trifluoro-m-toluene-sulfonamide; melting point 197°–198° C.

EXAMPLE 21

In analogy to Example 1, from N-[6-chloro-5-(p-chloro-phenyl)-4-pyrimidinyl]-α,α,α-trifluoro-o-toluenesulfonamide and ethylene glycol Na, there was obtained N-[5-(p-chlorophenyl)-6-(2-hydroxyethoxy)-4-pyrimidinyl]-α,α,α-trifluoro-o-toluene-sulfonamide, melting point 182°–184° C. (from CH₃CN-isopropyl ether).

The starting material was prepared from 4,6-dichloro-5-(p-chlorophenyl)pyrimidine and α,α,α-trifluoro-o-toluenesulfon-amide; melting point 191°–193° C. (from CH₃CN).

EXAMPLE 22

In analogy to Example 1, from N-[6-chloro-5-(p-ethyl-phenyl)-4-pyrimidinyl]-p-isopropylbenzenesulfonamide and ethylene glycol Na, there was obtained N-[6-(2-hydroxyethoxy)-5-(p-ethylphenyl)-4-pyrimidinyl]-p-isopropyl]benzene-sulfonamide, melting point 137°–138° C. (from acetonitrile and isopropyl ether).

The starting material was prepared as follows:

From diethyl (p-ethylphenyl)malonate and formamidine acetate, there was obtained 5-(p-ethyl)-4,6(1H,5H)-pyrimidinedione, melting point >270° C., and therefrom with POCl₃, there was obtained 4,6-dichloro-5-(p-ethylphenyl)pyrimidine, melting point 48°–49° C. (from n-hexane).

Reaction of this compound with p-isopropylbenzenesulfonamide yielded N-[6-chloro-5-(p-ethylphenyl)-4-pyrimidinyl]-p-isopropylbenzenesulfonamide, melting point 187°–188° C. (from acetonitrile and isopropyl ether).

EXAMPLE 23

In analogy to Example 1, from N-[6-chloro-5-(p-chlorophenyl)-4-pyrimidinyl]-2-naphthalenesulfonamide and ethylene glycol Na, there was obtained N-[5-(p-chlorophenyl)-6-(2-hydroxyethoxy)-4-pyrimidinyl]-2-naphthalenesulfonamide, melting point 196°–198° C. (from CH₃CN and isopropyl ether).

The starting material was prepared from 4,6-dichloro-5-(p-chlorophenyl)pyrimidine and 2-naphthalenesulfonamide; melting point 265°–269° C. (from CH₃CN).

EXAMPLE 24

In analogy to Example 1, from p-chloro-N-[6-chloro-5-(m-nitrophenyl)-4-pyrimidinyl]benzenesulfonamide and ethylene glycol Na, there was obtained p-chloro-N-[6-(2-hydroxyethoxy)-5-(m-nitrophenyl)-4-pyrimidinyl]benzenesulfonamide, melting point 186°–187° C. (from CH₃CN and isopropyl ether).

The starting material was prepared from 4,6-dichloro-5-(m-nitrophenyl)pyrimidine and p-chlorophenylsulfonamide; melting point 261°–263° C. (from CH₃CN).

EXAMPLE 25

In analogy to Example 1, from N-[6-chloro-5-(m-nitrophenyl)-4-pyrimidinyl]-α,α,α-trifluoro-p-toluenesulfonamide and ethylene glycol Na, there was obtained α,α,α-trifluoro-N-[6-(2-hydroxyethoxy)-5-(m-nitrophenyl)-4-pyrimidinyl]-p-toluenesulfonamide, melting point 194°–195° C. (from ethyl acetate/n-hexane).

The starting material was prepared from 4,6-dichloro-5-(m-nitrophenyl)pyrimidine and α,α,α-trifluoro-p-toluenesulfonamide; melting point 246°–250° C. (from CH₃CN).

EXAMPLE 26

In analogy to Example 1, from p-(benzyloxy)-N-[6-chloro-5-(p-chlorophenyl)-4-pyrimidinyl]benzenesulfonamide and ethylene glycol Na, there was obtained p-(benzyloxy)-N-[5-(p-chlorophenyl)-6-(2-hydroxyethoxy)-4-pyrimidinyl]benzene-sulfonamide, melting point 162°–163° C. (from acetone and isopropyl ether).

The starting material was prepared from 4,6-dichloro-5-(p-chlorophenyl)pyrimidine and p-(benzyloxy)benzenesulfon-amide; melting point 233°–236° C. (from acetone and ethyl acetate).

EXAMPLE 27

A solution of 512 mg of p-(benzyloxy)-N-[5-(p-chlorophenyl)-6-(2-hydroxyethoxy)-4-pyrimidinyl]benzene-sulfonamide in 30 ml of glacial acetic acid was treated with 2 ml of 4N HCl in dioxane and 100 mg of 10% palladium-carbon. The mixture was hydrogenated while stirring, thereafter the solution was suction filtered, evaporated under reduced pressure and the residue was recrystallized from isopropyl ether and again from CH₃CN. There was obtained N-[5-(p-chlorophenyl)-4-pyrimidinyl]-p-hydroxybenzenesulfonamide, melting point 231°–232° C.

EXAMPLE 28

In analogy to Example 1, from N-[6-chloro-5-(p-chlorophenyl)-4-pyrimidinyl]-p-(2-methoxyethoxy)benzenesulfon-amide and ethylene glycol Na, there was obtained N-[5-(p-chlorophenyl)-6-(2-hydroxyethoxy)-4-pyrimidinyl]-p-(2-methoxyethoxy)benzenesulfonamide, melting point 151°–152° C. (from CH₃CN and isopropyl ether).

The starting material was prepared from 4,6-dichloro-5-(p-chlorophenyl)pyrimidine and p-(2-methoxyethoxy)benzenesulfonamide; melting point 212°–215° C. (from CH₃CN).

EXAMPLE 29

In analogy to Example 1, from N-[5-(p-bromophenyl)-6-chloro-4-pyrimidinyl]-p-chlorobenzenesulfonamide and ethylene glycol Na, there was obtained N-[5-(p-bromophenyl)-6-(2-hydroxyethoxy)-4-pyrimidinyl]-p-chlorobenzenesulfonamide, melting point 179°–180° C. (from acetone and isopropyl ether).

The starting material was prepared as follows:

In analogy to Example 3, paragraph a), from diethyl p-bromophenylmalonate and formamidine acetate there was obtained 5-(p-bromophenyl)-4,6(1H,5H)-pyrimidinedione, melting point >270° C. The compound was used in the next step after drying under reduced pressure at 80° C. overnight.

In analogy to Example 3, paragraph b), from 5-(p-bromophenyl)-4,6(1H,5H)-pyrimidinedione and POCl₃, there was prepared 5-(p-bromophenyl)-4,6-dichloropyrimidine, melting point 99°–100° C. (from hexane), and therefrom with p-chlorophenylsulfonamide, there was prepared N-[5-(p-bromophenyl)-6- chloro-4-pyrimidinyl]-p-chlorobenzenesulfonamide, melting point 266°–268° C. (from CH₃CN).

EXAMPLE 30

In analogy to Example 1, from p-chloro-N-(6-chloro-5-p-tolyl-4-pyrimidinyl)benzenesulfonamide and ethylene glycol Na, there was obtained p-chloro-N-[6-(2-hydroxyethoxy)-5-p-tolyl-4-pyrimidinyl]benzenesulfonamide, melting point 162°–165° C. (from acetone and isopropyl ether).

The starting material was prepared as follows:

In analogy to Example 3, paragraph a), from diethyl p-tolylmalonate and formamidine acetate, there was prepared 5-p-tolyl-4,6-(1H,5H)-pyrimidinedione, melting point >270° C. The substance was used in the next step after drying under reduced pressure at 80° C.

In analogy to Example 3, paragraph b), from 5-p-tolyl-4,6(1H,5H)-pyrimidinedione and POCl₃, there was prepared 4,6-dichloro-5-p-tolylpyrimidine, melting point 81°–82° C. (from hexane), and therefrom with p-chlorophenylsulfonamide, there was prepared p-chloro-N-(6-chloro-5-p-tolyl-4-pyrimidinyl)-benzenesulfonamide, melting point 229°–230° C. (from acetonitrile).

EXAMPLE 31

A solution of 237 mg of N-[5-(p-chlorophenyl)-6-(2-hydroxyethoxy)-4-pyrimidinyl]-α,α,α-trifluoro-p-toluenesulfonamide in 5 ml of methanol was treated with 27.0 mg of sodium methylate and thereafter with 5 ml of isopropyl ether. The white precipitate was removed by filtration under suction and dried at 50° C. under reduced pressure. There was obtained N-[5-(p-chlorophenyl)-6-(2-hydroxyethoxy)-4-pyrimidinyl]-α,α,α-trifluoro-p-toluenesulfonamide sodium salt as a white solid.

EXAMPLE 32

60 mg of sodium were added to 2 ml of ethylene glycol at 70° C. Thereafter, 223 mg of N-[6-chloro-5-(2,6-dimethoxybenzyl)-4-pyrimidinyl]-p-vinyl-benzenesulfonamide were added and the reaction mixture was heated at 150° C. for 4.5 hours. The ethylene glycol was distilled under reduced pressure, the residue was taken up in EtOAc/H₂O and extracted once with ethyl acetate. Thereafter, the aqueous phase was acidified with 1N HCl and extracted four times with ethyl acetate. The organic phase was dried, filtered and concentrated under reduced pressure. The residue was chromatographed over 50 g of SiO₂ with methylene chloride/ethyl acetate 1:1. There were obtained 50 mg of N-[5-(2,6-dimethoxybenzyl)-6-(2-hydroxyethoxy)-4-pyrimidinyl]-p-vinylbenzenesulfonamide, melting point 138°–139° C.

The starting material was prepared as follows:

a) A mixture of 1.52 ml of diethyl malonate, 1.66 g of 2,6-dimethoxybenzaldehyde, 0.1 ml of piperidine, 0.11 ml of glacial acetic acid and 100 ml of toluene was boiled at 110° C. on a water separator for 3.5 hours. The solution was extracted with 10% NaHCO₃ solution and back-washed with saturated NaCl solution. The organic phase was dried, filtered under suction and evaporated under reduced pressure. There were obtained 2.8 g of diethyl (2,6-dimethoxybenzylidene)malonate, as a dark yellow oil.

b) A mixture of 2.8 g of diethyl (2,6-dimethoxybenzylidene)malonate, 0.6 g of palladium-carbon, 50 ml of methanol and 50 ml of glacial acetic acid was stirred at 25° C. overnight. The solution was filtered and concentrated, and the residue was taken up in ethyl acetate and extracted with 20% NaHCO₃ and some ice. Thereafter, the mixture was extracted with 1N, HCl, back-washed with saturated NaCl solution, the organic phase was dried and evaporated under reduced pressure. The crude product was distilled in a high vacuum at 170° C./0.6 mbar. 2.1 g of diethyl (2,6-dimethoxybenzyl)malonate were obtained.

c) 0.23 g of formamidine acetate in 15 ml of ethanol was added to 0.14 g of sodium in 15 ml of ethanol. The reaction mixture was stirred 25° C. for 30 minutes and treated dropwise with 0.62 g of diethyl (2,6-dimethoxybenzyl)malonate in 10 ml of ethanol. Starting material was no longer present after 2 days. The residue was removed by filtration under suction, dissolved in a small amount of water and acidified with 1N HCl. The precipitated crystals were removed by filtration under suction and dried at 90° C. in a high vacuum. There was obtained 0.175 g of 5-(2,6-dimethoxy-benzyl)-4,6-pyrimidinediol of melting point >245° C.

d) A mixture of 1.04 g of 5-(2,6-dimethoxybenzyl)-4,6-pyrimidinediol and 12 ml of phosphorus oxychloride was boiled at reflux at 85° C. for 3 hours. The reaction solution was poured on to ice and extracted twice with methylene chloride. The organic phase was back-washed with saturated NaCl solution, dried, filtered and concentrated under reduced pressure. The crude product was recrystallized from toluene/n-hexane. There was obtained 0.41 g of 4,6-dichloro-5-(2,6-dimethoxybenzyl)-pyrimidine, melting point 152°–153° C.

e) A mixture of 80 mg of 4,6-dichloro-5-(2,6-dimethoxybenzyl)pyrimidine and 170 mg of p-vinylbenzenesulfonamide monopotassium salt (J. Am. Chem. Soc. 1956, 78, 2169) from the corresponding sulfonamide with potassium t-butylate in absolute MeOH and 10 ml of dimethylformamide was heated at 100° C. for 6 hours. Thereafter, the mixture was left to cool to 25° C. overnight. Now, 30 ml of 0.5N HCl were added to the reaction solution while stirring. The precipitated substance was removed by filtration under suction and recrystallized from toluene/n-hexane. There were obtained 25 mg of N-(6-chloro-5-(2,6-dimethoxy-benzyl)-4-pyrimidinyl)-p-vinylbenzenesulfonamide, melting point 197°–198° C.

EXAMPLE 33

29 mg of sodium were added portionwise to 10 ml of ethylene glycol (freshly distilled over Na) while excluding moisture. Thereafter, 123 mg of N-[6-chloro-6-[o-(trifluoro-methyl)benzyl]-4-pyrimidinyl]-α,α,α-trifluoro-p-toluenesulfon-amide were added and the reaction mixture was heated at 150° C. for 3 hours. Thereafter, the excess ethylene glycol was evaporated under reduced pressure; the residue was dissolved in water and washed with ethyl acetate. The aqueous phase was adjusted to pH 3.0 with 1N hydrochloric acid and extracted with ethyl acetate. The organic phase was washed with water and saturated sodium chloride solution, dried and evaporated under reduced pressure. The residue was chromatographed over 30 g of SiO₂ with methylene chloride/ethyl acetate (1:1). There was obtained α,α,α-trifluoro-N-[6-(2-hydroxyethoxy)-6-[o-(trifluoro-methyl)benzyl]pyrimidinyl]-p-toluenesulfonamide as a white foam. MS: 521 (M); 456 (M—SO₂+H).

The starting material was prepared as follows:

a) A solution of 30 ml of phosphorus tribromide in 60 ml of absolute toluene was added dropwise at 20°-30° C. to a solution of 14 g of o-trifluoromethylbenzyl alcohol in 80 ml of absolute toluene. Subsequently, the reaction mixture was stirred at room temperature for 2 hours, the toluene was distilled under reduced pressure, the residue was dissolved in methylene chloride, treated with water and the mixture was adjusted to pH 8.0 with potassium hydrogen carbonate. The aqueous phase was extracted three times with $CH_2Cl_2$ and the organic phases were washed twice with water and once with saturated NaCl solution, dried over $Na_2SO_4$ and evaporated under reduced pressure. o-Trifluoromethylbenzyl bromide was obtained as the residue.

b) 40 ml of diethyl malonate in 350 ml of ethyl alcohol were treated portionwise with 18.6 g of sodium ethylate at room temperature and the mixture was then treated with 12 g of o-trifluoromethylbenzyl bromide within 30 minutes. The reaction mixture was stirred at room temperature overnight. The alcohol was distilled under reduced pressure and the residue was dissolved in ethyl acetate. The solution was washed twice with water and once with NaCl solution, dried under reduced pressure and evaporated. The residue was chromatographed over 300 g of $SiO_2$ with $CH_2Cl_2$/AcOEt 95:5 and yielded 11 g of diethyl [o-(trifluoromethyl)benzyl]malonate as a colourless oil.

c) 0.63 g of formamidine acetate in 40 ml of absolute ethyl alcohol was treated with 1.2 g of sodium ethylate at room temperature, stirred at room temperature for 30 minutes and then treated dropwise at room temperature with a solution of 1.6 g of diethyl [o-(trifluoromethyl)benzyl]malonate in 8 ml of absolute ethyl alcohol. After stirring at 50° C. for 4 hours, the reaction mixture was worked-up and yielded 5-[o-(trifluoro-methyl)benzyl]-4,6(1H,5H)pyrimidinedione, melting point >290° C.

d) From 5-[o-(trifluoromethyl)benzyl]-4,6(1H,5H)pyrimidinedione and phosphorus oxychloride, there was prepared 5-[o-(trifluoromethyl)benzyl]-4,6-dichloropyrimidine, melting point 60°-63° C.

e) 295 mg of 4,6-dichloro-5-[o-(trifluoromethyl)benzyl]pyrimidine in 10 ml of freshly distilled dimethyl sulfoxide were treated with 342 mg of $\alpha,\alpha,\alpha$-trifluoro-p-toluenesulfonamide monopotassium salt (from the corresponding sulfonamide with KOH and abs. ethyl alcohol) and stirred at 150° C. for 5 hours. After completion of the reaction, the solvent was distilled under reduced pressure. The residue was dissolved in ethyl acetate and the solution was washed with 10% potassium bicarbonate solution, 0.5N HCl, water and NaCl solution. The organic phase was dried and evaporated under reduced pressure. The residue was chromatographed over 30 g of $SiO_2$ using ethyl acetate and yielded 135 mg of N-[6-chloro-6-[o-(trifluoro-methyl)benzyl]-4-pyrimidinyl]-$\alpha,\alpha,\alpha$-trifluoro-p-toluene-sulfonamide as a white foam. MS: 495 (M), 431 (—$SO_2$), 430 (—$SO_2$+H), 362 (—$CF_3$+$SO_2$).

EXAMPLE 34

In analogy to Example 33, from N-[6-chloro-5-[o-(trifluoromethyl)benzyl]-4-pyrimidinyl]-p-methoxybenzenesulfonamide and ethylene glycol Na, there was obtained N-[6-(2-hydroxy-ethoxy)-5-[o-(trifluoromethyl)benzyl]-4-pyrimidinyl]-p-methoxybenzenesulfonamide, melting point 100°-107° C.

The starting material was prepared as follows:

In analogy to Example 33, paragraph e), from 4,6-dichloro-5-[o-(trifluoromethyl)benzyl]pyrimidine and p-methoxybenzenesulfonamide K salt, there was obtained N-[6-chloro-5-[o-(trifluoromethyl)benzyl]-4-pyrimidinyl]-p-methoxybenzenesulfonamide as a white foam, melting point 68°-70° C.

EXAMPLE 35

In analogy to Example 33, from p-chloro-N-[6-chloro-5-[o-(trifluoromethyl)benzyl]-4-pyrimidinyl]-benzenesulfonamide and ethylene glycol Na, there was obtained p-chloro-N-[6-(2-hydroxyethoxy)-5-[o-(trifluoromethyl)benzyl]-4-pyrimidinyl]benzenesulfonamide, melting point 134°-135° C.

The starting material was prepared in analogy to Example 33, paragraph e), from 4,6-dichloro-5-[o-(trifluoromethyl)benzyl]pyrimidine and p-chlorobenzenesulfonamide K salt; melting point >210° C. (decomposition).

EXAMPLE 36

In analogy to Example 33, from N-[6-chloro-5-(o-methoxybenzyl)-4-pyrimidinyl]-p-vinylbenzenesulfonamide and ethylene glycol Na, there was obtained N-[6-(2-hydroxyethoxy)-5-(o-methoxybenzyl)-4-pyrimidinyl]-p-vinylbenzenesulfonamide, melting point 93°-102° C.

The starting material was prepared in analogy to Example 33, paragraph e) from 4,6-dichloro-5-(o-methoxybenzyl)pyrimidine and p-vinylbenzenesulfonamide K salt; melting point 125°-129° C.

EXAMPLE 37

In analogy to Example 33, from N-[6-chloro-5-[o-(trifluoromethyl)benzyl]-4-pyrimidinyl]-p-(methylthio)-benzenesulfon-amide and ethylene glycol Na there was obtained N-[6-(2-hydroxyethoxy)-5-[o-(trifluoromethyl)benzyl]-4-pyrimidinyl]-p-(methylthio)benzenesulfonamide as a yellowish resin.

The starting material was prepared in analogy to Example 33, paragraph e), from 4,6-dichloro-5-[o-(trifluoromethyl)]benzylpyrimidine and p-(methylthio)-benzenesulfonamide; IR: 3433 cm$^{-1}$ (NH); 1313 ($SO_2$); 1137 and 1094 ($F_3C$).

EXAMPLE 38

In analogy to Example 32, from N-[6-chloro-5-(2,4-dimethoxybenzyl)-4-pyrimidinyl]-p-isopropylbenzenesulfon-amide, ethylene glycol and sodium, there was obtained N-[5-(2,4-dimethoxybenzyl)-6-(3-hydroxypropyl)-4-pyrimidinyl]-p-isopropylbenzenesulfonamide, melting point 97° C.

The starting material was prepared as follows:

In analogy to Example 32, paragraph a), from 2,4-dimethoxybenzaldehyde, diethyl malonate, glacial acetic acid, piperidine and toluene, there was prepared diethyl (2,4-dimethoxybenzylidene)malonate. Therefrom in analogy to Example 32, paragraph b), there was prepared diethyl (2,4-dimethoxy-benzyl)malonate as a clear oil, boiling point 160° C./0.4 mbar.

In analogy to Example 32, paragraph e), from diethyl (2,4-dimethoxybenzyl)malonate, formamidine acetate and the Na salt of ethanol, there was prepared 5-(2,4-dimethoxybenzyl)-4,6-pyrimidinediol and therefrom in analogy to Example 32, paragraph d), there was prepared 4,6-dichloro-5-(2,4-dimethoxybenzyl)pyrimidine, melting point 130°-131° C.

In analogy to Example 32, paragraph e), from 4,6-dichloro-5-(2,4-dimethoxybenzyl)pyrimidine, p-isopropylbenzenesulfon-amide K (from the corresponding sulfonamide with potassium t-butylate in absolute MeOH) and DMSO, there was finally prepared N-[6-chloro-5-(2,4-dimethoxybenzyl)-4-pyrimidinyl]-p-isopropylbenzenesulfonamide, melting point 132°-134° C.

EXAMPLE 39

A solution of 110 mg of N-[6-(2-hydroxyethoxy)-5-(o-methoxybenzyl)-4-pyrimidinyl]-p-vinylbenzenesulfonamide in 3 ml of absolute tetrahydrofuran was treated with 0.3 ml of 3,4-dihydro-2H-pyran and 4 drops of trifluoroacetic acid. After boiling under reflux overnight, the solvent was distilled under reduced pressure and the residue was chromatographed on silica gel with methylene chloride/ethyl acetate (9:1). There were obtained 100 mg of rac-N-[5-(o-methoxybenzyl)-6-[2-[(tetrahydro-2H-pyran-2-yl)oxy]ethoxy]-4-pyrimidinyl]-p-vinylbenzenesulfonamide as a white resin, MS: 460 (M—SO$_2$+H); 430 (M—SO$_2$+OCH$_3$).

EXAMPLE 40

318 mg of rac-N-[5-(o-methoxybenzyl)-6-[2-[(tetrahydro-2H-pyran-2-yl)oxy]ethoxy]-4-pyrimidinyl]-p-vinylbenzenesulfonamide, 5.3 mg of osmium tetroxide and 270 mg of sodium(meta)periodate were added in succession to a mixture of 1.5 ml of water and 4 ml of dioxane at room temperature. After stirring at room temperature for 1 hour, the dioxane was distilled under reduced pressure. Thereafter, the aqueous phase was extracted three times with ethyl acetate. The ethyl acetate was washed twice with water and once with NaCl solution (saturated), dried and distilled under reduced pressure. The residue was chromatographed over 30 g of SiO$_2$ with CH$_2$Cl$_2$/ethyl acetate and yielded 150 mg of rac-p-[[5-(o-methoxybenzyl)-6-[2-[(tetra-hydro-2H-pyran-2-yl)oxy]ethoxy]-4-pyrimidinyl]sulfamoyl]-benzaldehyde as white foam. MS: 527 (M); 443

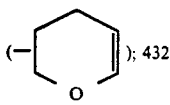 ); 432

(—OCH$_3$+SO$_2$).

EXAMPLE 41

170 mg of rac-p-[[5-(o-methoxybenzyl)-6-[2-[(tetrahydro-2H-pyran-2-yl)oxy]ethoxy]-4-pyrimidinyl]sulfamoyl]benzaldehyde and, after 30 minutes, 1 ml of absolute tetrahydrofuran were added at room temperature to a Grignard solution prepared from 60 mg of magnesium and 0.15 ml of methyl iodide in diethyl ether. After stirring at room temperature for 3 hours, the reaction was interrupted by the addition of saturated ammonium chloride solution. The reaction mixture was diluted with ethyl acetate and the aqueous phase was extracted twice with ethyl acetate. The organic phase was washed with water and saturated NaCl solution, dried and evaporated under reduced pressure. The residue was chromatographed over 35 g of SiO$_2$ with CH$_2$Cl$_2$/ethyl acetate (8:2) and (1:1) and yielded 135 mg of p-[(RS)-1-hydroxyethyl]-N-[5-(methoxybenzyl)-6-[2-[[(RS)-tetrahydro-2H-pyran-2-yl]oxy]ethoxy]-4-pyrimidinyl]benzene-sulfonamide melting point >56° C. (sublimation).

EXAMPLE 42

53 mg of rac-p-[[5-(o-methoxybenzyl)-6-[2-[(tetrahydro-2H-pyran-2-yl)oxy]ethoxy]-4-pyrimidinyl]sulfamoyl]benzalde-hyde were dissolved in 3 ml of methyl alcohol and treated with 37 mg of sodium borohydride at room temperature. After stirring at room temperature for 1 hour, the methanol was evaporated under reduced pressure. The residue was dissolved in ethyl acetate, washed with water and NaCl solution (saturated), dried and distilled under reduced pressure. There were obtained 42 mg of rac-α-hydroxy-N-[5-(o-methoxybenzyl)-6-[2-[(tetra-hydro-2H-pyran-2-yl)oxy]ethoxy]-4-pyrimidinyl]-p-toluene-sulfonamide as a colorless oil. MS: 529 (M); 445 (tetrahydro-2H-pyran-2-yl); 434 (—OCH$_3$+SO$_2$).

EXAMPLE 43

53 mg of rac-p-[[5-(o-methoxybenzyl)-6-[2(tetrahydro-2H-pyran-2-yl]oxy]ethoxy]-4-pyrimidinyl]sulfamoyl]benzalde-hyde were dissolved in 3 ml of ethyl alcohol and treated at room temperature with 7 mg of hydroxylamine hydrochloride and 14 g of finely powdered potassium carbonate. After stirring at room temperature for 3 hours, the ethanol was distilled under reduced pressure. The residue was dissolved in ethyl acetate and washed with water and NaCl solution (saturated). The organic phase was dried and evaporated under reduced pressure, whereby rac-α-[(>E/Z)-hydroxyimino-N-[5-(o-methoxybenzyl)-6-[2-[(tetrahydro-2H-pyran-2-yl)oxy]ethoxy]-4-pyrimidinyl]-p-toluenesulfonamide, melting point 49°-52° C., was obtained.

EXAMPLE 44

A solution of 60 mg of p-[(RS-1-hydroxyethyl]-N-[5-(o-methoxybenzyl)-6-[2-[[(RS)-tetrahydro-2H-pyran-2-yl]oxy]ethoxy]-4-pyrimidinyl]benzenesulfonamide in 3 ml of tetrahydrofuran was treated with 2 drops of 3N HCl. After stirring at room temperature for 4 hours, the reaction mixture was evaporated under reduced pressure. The residue was chromatographed on silica gel with methylene chloride/ethyl acetate (1:1) and ethyl acetate and yielded rac-N-[6-(2-hydroxyethoxy)-5-(o-methoxybenzyl)-4-pyrimidinyl]-p-(1-hydroxyethyl)benzenesulfonamide as a white resin. MS: 459 (M), 394 (—SO$_2$/H), 364 (—SO$_2$/OCH$_3$).

EXAMPLE 45

In analogy to Example 44, from rac-a-[(E/Z)-hydroxyimino]-N-[5-(o-methoxybenzyl)-6-[2-[(tetrahydro-2H-pyran-2-yl)oxy]ethoxy]-4-pyrimidinyl]-p-toluenesulfonamide, there was obtained α-[(E/Z)-hydroxyimino]-N-[6-(2-hydroxyethoxy)-5-(o-methoxybenzyl)-4-pyrimidinyl]-p-toluenesulfonamide as a yellow resin. IR: 3403 and 3193 cm$^{-1}$ (W, OH), 2607 (W, NH); 1729 (W, C=N).

EXAMPLE 46

In analogy to Example 44, from rac-α-hydroxy-N-[5-(o-methoxybenzyl)-6-[2-[(tetrahydro-2H-pyran-2-yl)oxy]ethoxy]-4-pyrimidinyl]-p-toluenesulfonamide, there was obtained α-hydroxy-N-[6-(2-hydroxyethoxy)-5-(o-methoxybenzyl)-4-pyrimidinyl]-p-toluenesulfonamide as a pale brown resin. MS: 445 (M), 380 (—SO$_2$/H), 274.

EXAMPLE 47

In analogy to Example 44, from rac-p-[[5-(o-methoxy-benzyl)-6-[2-[(tetrahydro-2H-pyran-2-yl)oxy]ethoxy]-4-pyrimidinyl]-sulfamoylbenzaldehyde, there was obtained p-[[6-(2-hydroxy-ethoxy)-5-(o-methoxybenzyl)-4-pyrimidinyl]sulfamoyl]benzaldehyde as a while resin. MS: 443 (M), 348 (—SO$_2$/OCH$_3$), 274.

EXAMPLE 48

208 mg of N-[6-(2-hydroxyethoxy)-5-(o-methoxybenzyl)-4-pyrimidinyl]-p-vinylbenzenesulfonamide were dissolved in 3 ml of absolute THF, treated with 0.06 ml of pyridine and 0.07 ml of acetic anhydride and boiled under reflux for 3 hours. After distilling the solvent under reduced pressure, the residue was dissolved in ethyl acetate. The solution was washed with water and sodium chloride solution, dried and evaporated. After chromatography over silica gel with methylene chloride and methylene chloride/ethyl acetate (19:1 and 9:1), the residue yielded 2-[[5-(o-methoxybenzyl)-6-[(p-vinylphenyl)sulfamoyl]-4-pyrimidinyl]oxy]ethyl acetate as a white resin.

EXAMPLE 49

In analogy to Example 1, from N-[6-chloro-5-($\alpha,\alpha,\alpha$-trifluoro-p-tolyl)-4-pyrimidinyl]-p-isopropylbenzenesulfonamide and ethylene glycol Na there, was obtained N-[6-(2-hydroxyethoxy)-5-($\alpha,\alpha,\alpha$-trifluoro-p-tolyl)-4-pyrimidinyl]-p-isopropylbenzenesulfonamide, melting point 222°-223° C. (from acetone and isopropyl ether).

The starting material was prepared from 4,6-dichloro-5-$\alpha,\alpha,\alpha$-trifluoro-p-tolylpyrimidine and p-isopropylbenzene-sulfonamide, melting point 266°-269° C. (from acetonitrile).

EXAMPLE 50

190 mg of N-[6-chloro-5-(p-methoxyphenyl)-4-pyrimidinyl]-p-toluenesulfonamide were added to a sodium glycolate solution from 46 mg of sodium in 1 ml of ethylene glycol. After a reaction period of 5 hours at 100° C., the reaction mixture was evaporated to dryness under reduced pressure. The residue was partitioned between ethyl acetate and 1N hydrochloric acid. The organic phase was washed neutral, dried and evaporated under reduced pressure. The residue was chromatographed on silica gel with methylene chloride and ethyl acetate (4:1 v/v). There were obtained 175 mg of N-[6-(2-hydroxy-ethoxy)-5-(p-methoxyphenyl)-4-pyrimidinyl]-p-toluenesulfon-amide, melting point 147°-149° C. (from methylene chloride/hexane).

The starting material was prepared as follows:

150 ml of ethyl orthoformate and 1 g of methanesulfonic acid were added to a solution of 41.55 g of p-methoxyphenyl-acetic acid in 150 ml of absolute ethanol. The reaction mixture was heated at 85° C. for 20 hours. The ethyl formate formed was distilled continuously from the reaction mixture. Thereafter, the reaction mixture was neutralized with sodium ethylate. The solvent was evaporated and the residue was taken up in methylene chloride and distilled. There were obtained 46.7 g of ethyl (p-methoxy)phenylacetate as a colorless liquid, boiling point 84° C./0.025 Torr.

7.5 g of sodium ethylate and 120 ml of diethyl carbonate were added to 19.4 g of the previously obtained ester. The suspension obtained was stirred vigorously at 130° C. and the ethanol formed was distilled from the reaction mixture. Thereafter, the reaction mixture was cooled to room temperature and poured on to ice and aqueous hydrochloric acid (10% excess). After extraction with ethyl acetate and working-up the extract, the product was purified by distillation. There were obtained 25 g of diethyl (p-methoxy)phenylmalonate, boiling point 115° C./0.05 Torr.

10.9 g of sodium ethylate were suspended in 125 ml of dry ethanol. 4.83 g of formamidine hydrochloride and 13.3 g of the malonic ester obtained in the preceding paragraph were added thereto while cooling with ice. The reaction mixture was stirred at room temperature for 3 hours with the exclusion of moisture. Thereafter, the solvent was evaporated. The residue was dissolved in 100 ml of water, and the aqueous phase was washed with toluene and acidified. There were obtained 8 g of 5-(p-methoxy)phenyl-6-hydroxy-4(3H)-pyrimidinone, melting point >250° C.

1 g of the pyrimidinone described in the foregoing paragraph was suspended in 5 ml of phosphorus oxychloride. The suspension was stirred at 80° C. with the exclusion of moisture, whereby a clear solution was obtained. After 30 minutes, the excess reagent was distilled and the residue was taken up in methylene chloride and shaken with aqueous potassium hydrogen carbonate solution until the evolution of carbon dioxiode no longer occurred. After evaporation of the solvent, the residue was filtered over silica gel with methylene chloride. There was obtained 0.7 g of 4,6-dichloro-5-(p-methoxyphenyl)pyrimidine, melting point 95°-96° C.

5.15 g of p-toluenesulfonamide dissolved in ethanol were added to a boiling ethanolic potassium hydroxide solution (2 g of 85% potassium hydroxide in 50 ml of abs. ethanol). Thereafter, 50 ml of absolute benzene were added and the majority of the solvent mixture was distilled at normal pressure. 4.6 g of p-toluene-sulfonamide potassium were obtained. 510 mg of the dichloropyrimidine described in the previous paragraph and 840 mg of p-toluenesulfonamide potassium were dissolved in 3 ml of dry dimethylformamide. The solution was held at 120° C. for 3 hours. Thereafter, the dimethylformamide was distilled. The residue was partitioned between ethyl acetate and 1N hydrochloric acid. The organic phase was washed neutral and evaporated. After the addition of methanol, there were obtained 540 mg of N-[6-(chloro-5-(p-methoxyphenyl)-4-pyrimidinyl]-p-toluenesulfonamide, melting point 210°-212° C.

EXAMPLE 51

In analogy to Example 50, from 300 mg of N-[6-chloro-5-(p-methoxyphenyl)-4-pyrimidinyl]-p-methoxybenzenesulfon-amide, there were obtained 200 mg of N-[6-(2-hydroxyethoxy)-5-(p-methoxyphenyl)-4-pyrimidinyl]-p-methoxybenzene-sulfonamide, melting point 132°-134° C.

The starting material was prepared as follows:

25 ml of 25% NH$_4$OH were added dropwise while cooling in an ice bath to a solution of 7.3 g of p-methoxybenzenesulfonyl chloride in 50 ml of tetrahydrofuran. Subsequently, the reaction mixture was stirred vigorously for 30 minutes at 70° C. (bath temperature). Thereafter, the tetrahydrofuran was distilled. The residue was extracted with ethyl acetate. There was obtained p-methoxybenzenesulfonamide which was converted into the potassium salt as described in Example 50.

A solution of 510 mg of 4,6-dichloro-5-(p-methoxyphenyl)pyrimidine and 680 mg of p-methoxybenzenesulfonamide potassium in 3 ml of dimethylformamide was heated at 130° C. for 1 hour. After working-up the reaction mixture, there were obtained 690 mg of N-[6-chloro-5-(p-methoxyphenyl)-4-pyrimidinyl]-p-methoxybenzenesulfonamide, melting point 165°-167° C.

EXAMPLE 52

In analogy to Example 50, from N-[6-chloro-5-(p-methoxyphenyl)-4-pyrimidinyl]-p-(methylthio)benzenesulfonamide, there was obtained N-[6-(2-hydroxyethoxy)-5-(p-methoxyphenyl)-4-pyrimidinyl]-p-(methylthio)benzenesulfonamide, melting point 171°-172° C.

The starting material was prepared as described in Example 50 from 4,6-dichloro-5-(p-methoxy)phenylpyrimidine and (p-methylthio)benzenesulfonamide potassium, melting point 204°-205° C.

EXAMPLE 53

In analogy to Example 50, from N-[6-chloro-5-(p-methoxyphenyl)-2-methyl-4-pyrimidinyl]-p-methoxybenzenesulfon-amide, there was obtained N-[6-(2-hydroxyethoxy)-5-(p-methoxy-phenyl)-2-methyl-4-pyrimidinyl]-p-methoxybenzenesulfon-amide, melting point 138°-139° C.

The starting material was prepared as follows:

2.94 g of acetamidine hydrochloride and 6.9 g of diethyl p-methoxyphenylmalonate were added to a solution of 5.6 g of sodium methylate in 75 ml of absolute ethanol. The reaction mixture was stirred at room temperature for 3 hours with the exclusion of moisture and at 50° C. for 1.5 hours. Thereafter, the ethanol was distilled. The residue was taken up in water and the suspension was acidified with 5N hydrochloric acid. The solid was filtered and washed with water until the wash solution had reached a pH of 4.5 to 5.7. The thus-obtained product was reacted with phosphorus oxychloride and yielded 2.8 g of 4,6-dichloro-2-methyl-(p-methoxy)phenylpyrimidine, melting point 114°-116° C. Reaction of this compound with p-methoxybenzene-sulfonamide potassium yielded N-[6-chloro-5-(p-methoxyphenyl)-2-methyl-4-pyrimidinyl]-p-methoxybenzenesulfon-amide, melting point 152°-154° C.

EXAMPLE 54

In analogy to Example 50, from 615 mg of N-[6-chloro-5-(p-methoxyphenyl)-4-pyrimidinyl]-p-isopropylbenzenesulfon-amide, there were obtained 550 mg N-[6-(2-hydroxyethoxy)-5-(p-methoxyphenyl)-4-pyrimidinyl]-p-isopropylbenzene-sulfonamide, melting point 128°-129° C.

In order to convert this sulfonamide into the sodium salt, 87 mg were dissolved in methanol, the stoichiometric amount of sodium methylate was added, the solvent was distilled and diisopropyl ether was added.

The starting material was prepared as follows:

p-Isopropylbenzenesulfonyl chloride, boiling point 105° C./0.25 Torr, was prepared from cumene and converted into the corresponding sulfonamide, melting point 104°-105° C. Reaction of 765 mg of 4,6-dichloro-5-(p-methoxyphenyl)-pyrimidine and 925 mg of p-isopropylbenzenesulfonamide potassium yielded 720 mg of N-[6-chloro-5-(p-methoxyphenyl)-4-pyrimidinyl]-p-isopropylbenzenesulfonamide, melting point 181°-182° C.

EXAMPLE 55

In analogy to Example 50, from 700 mg of p-t-butyl-N-[6-chloro-5-(p-methoxyphenyl)-4-pyrimidinyl]benzenesulfonamide, there were obtained 600 mg of p-t-butyl-N-[6-(2-hydroxy-ethoxy)-5-(p-methoxyphenyl)-4-pyrimidinyl] benzenesulfon-amide, melting point 165°-166° C.

The starting material was obtained from p-t-butylbenzenesulfonamide potassium and 4,6-dichloro-5-(p-methoxyphenyl)pyrimidine, melting point 204°-205° C.

EXAMPLE 56

In analogy to Example 50, from 216 mg of rac-p-sec-butyl-N-[6-chloro-5-(p-methoxyphenyl)-4-pyrimidinyl]-benzenesulfonamide, there were obtained 185 mg of rac-p-sec-butyl-N-[6-(2-hydroxyethoxy)-5-(p-methoxyphenyl)-4-pyrimidinyl]-benzenesulfonamide, melting point 120°-122° C.

The starting material was prepared from rac-p-sec-butylbenzenesulfonamide potassium and 2,6-dichloro-5-(p-methoxyphenyl)pyrimidine, melting point 172°-173° C.

EXAMPLE 57

In analogy to Example 50, from 280 mg of N-[6-chloro-5-[(p-methylthio)phenyl]-4-pyrimidinyl]-p-isopropylbenzene-sulfonamide, there were obtained 240 mg of N-[6-(2-hydroxy-ethoxy)-5-[p-(methylthio)-phenyl]-4-pyrimidinyl]-p-isopropylbenzenesulfonamide, melting point 135°-136° C. (from diisopropyl ether).

The starting material was prepared as follows:

15.2 g of (p-methylthio)benzaldehyde were dissolved in 50 ml of isopropanol. 1.31 g of sodium borohydride in 150 ml of isopropanol were added dropwise to this solution within 0.5 hour while cooling in an ice bath. After stirring at room temperature for 1 hour, 5 ml of acetone were added and the solvent was subsequently distilled. The residue was partitioned between methylene chloride and water. After working-up, there was obtained (p-methylthio)benzyl alcohol, melting point 40°-41° C. (from isopropanol).

7.71 g of (p-methylthio)benzyl alcohol were dissolved in 25 ml of dry methylene chloride. 4 ml of $SOCl_2$ were added to this solution within 30 minutes, while cooling in an ice bath. After distilling the solvent and the excess reagent, the residue was filtered over silica gel with methylene chloride. After distillation, there were obtained 4.3 g of (p-methylthio)benzyl chloride, boiling point 92° C./0.05 Torr.

9 g of the benzyl chloride obtained in the preceding paragraph were added to a suspension of 10 g of potassium cyanide and 0.1 g of sodium iodide in 100 ml of dimethylformamide. The reaction mixture was stirred at 90° C. for 1 hour with the exclusion of moisture. Thereafter, the dimethylformamide was distilled and the residue was partitioned between toluene and water. Working-up of the organic phase yielded (p-methylthio)benzyl cyanide, melting point 28°-30° C.

12 g of (p-methylthio)benzyl cyanide were dissolved in 30 ml of ethylene glycol and treated with 9 g of NaOH (as a 30% solution). The reaction mixture was stirred at 140° C. for 3 hours. After cooling to room temperature the mixture was acidified with 25% hydrochloric acid, the precipitate was taken up in ethyl acetate and extracted with water. There were obtained 11.5 g of (p-methylthio)phenylacetic acid; melting point 94°-96° C.

11 g of the previously obtained acid were dissolved in 50 ml of abs. ethanol and 25 ml of ethyl orthoformate and 1 g of methanesulfonic acid. The formate formed during the reaction was distilled continuously. The reaction had finished after 4 hours. The acid catalyst was neutralized with a stoichiometric amount of sodium ethylate. The solvent was distilled. The residue was taken up in methylene chloride and filtered over silica gel. There were obtained 12 g of ethyl (p-methylthio)-phenylacetate, melting point 46°-47° C.

The previously obtained compound was converted into diethyl (p-methylthio)phenylmalonate in analogy to the procedure described in Example 50. Boiling point 120° C./0.05 Torr.

5-(p-Methylthio)phenyl-6-hydroxy-4(3H)-pyrimidinone was obtained from the previously obtained diethyl malonate in analogy to the procedure described in Example 50.

The previously described pyrimidinone was converted with sodium methylate into the dialkoxy compound from which 4,6-dichloro-5-(p-methylthio)phenyl-pyrimidine was obtained by reaction with phosphorus oxychloride.

N-[6-Chloro-5-[p-(methylthio)phenyl[-4-pyrimidinyl]-p-isopropylbenzenesulfonamide, melting point 193°-195° C., was obtained from the previously described 4,6-dichloro compound by reaction with p-isopropylbenzenesulfonamide potassium.

EXAMPLE 58

In analogy to Example 50, from 230 mg of N-[6-chloro-5-[p-(methylthio)phenyl]-4-pyrimidinyl]-α,α,α-trifluoro-p-toluenesulfonamide, there were obtained 160 mg of N-[6-(2-hydroxyethoxy)-5-[p-(methylthio)-phenyl]-4-pyrimidinyl]-α,α,α-trifluoro-p-toluenesulfonamide, melting point 266°-268° C.

The starting material was obtained from 4,6-dichloro-5-p-(methylthio)phenyl-pyrimidine and α,α,α-trifluoro-p-toluenesulfonamide potassium, melting point 250°-252° C.

EXAMPLE 59

300 mg of N-[6-chloro-5-(p-methoxybenzyl)-4-pyrimidinyl]-p-methoxybenzenesulfonamide were added to a sodium glycolate solution from 1 ml of dry ethylene glycol and 46 mg of sodium. The reaction mixture was heated at 125° C. for 4 hours under an argon atmosphere. Thereafter, the ethylene glycol was distilled under reduced pressure. The residue was partitioned between ethyl acetate and 1N hydrochloric acid. The organic phase was washed neutral, dried and evaporated. The residue was chromatographed on silica gel with methylene chloride/ethyl acetate (1:1 v/v). There were obtained 250 mg of N-[6-(2-hydroxyethoxy)-5-(o-methoxybenzyl)-4-pyrimidinyl]-p-methoxybenzenesulfonamide, melting point 161°-162° C.

The starting material was prepared as follows:

By Knoevenagel condensation of o-methoxybenzaldehyde with diethyl malonate, there was obtained diethyl o-methoxybenzylidenemalonate, boiling point 140° C./0.05 Torr.

Hydrogenation of the previously obtained compound in ethanol in the presence of palladium/carbon yielded diethyl o-methoxybenzylmalonate, boiling point 115° C./0.01 Torr.

Reaction of diethyl o-methoxybenzylmalonate with formamidine hydrochloride yielded 5-(o-methoxybenzyl)-6-hydroxy-4(3H)-pyrimidione from which, by reaction with phosphorus oxychloride, there was obtained 4,6-dichloro-5-(o-methoxybenzyl)pyrimidine, melting point 95°-96° C.

Reaction of 4,6-dichloro-5-(o-methoxybenzyl)-4-pyrimidine and p-methoxybenzenesulfonamide potassium yielded N-[6-chloro-5-(o-methoxybenzyl)-4-pyrimidinyl]-p-methoxybenzenesulfonamide, melting point 149°-151° C.

EXAMPLE 60

In analogy to Example 59, from N-[6-chloro-5-(o-chlorobenzyl)-4-pyrimidinyl]-p-toluenesulfonamide, there was obtained N-[6-(2-hydroxyethoxy)-5-(o-chlorobenzyl)-4-pyrimidinyl]-p-toluenesulfonamide.

The starting material was prepared as follows:

Diethyl malonate and o-chlorobenzyl chloride were converted into diethyl o-chlorobenzylmalonate, boiling point 115° C./0.55 Torr.

Condensation of diethyl o-chlorobenzylmalonate with formamidine yielded 5-(o-chlorobenzyl)-6-hydroxy-4(3H)-pyrimidinone which, by reaction with phosphorus oxychloride, yielded 4,6-chloro-5-(o-chlorobenzyl)pyrimidine, melting point 110°-112° C.

From 4,6-dichloro-5-(o-chlorobenzyl)pyrimidine and p-toluenesulfonamide potassium, there was obtained N-[6-chloro-5-(o-chlorobenzyl)-4-pyrimidinyl]-p-toluenesulfonamide which was used as the crude product.

EXAMPLE 61

In analogy to Example 59, from N-[6-chloro-5-(o-methoxybenzyl)-4-pyrimidinyl]-p-(methylthio)benzenesulfonamide, there was obtained N-[6-(2-hydroxyethoxy)-5-(o-methoxy-benzyl)-4-pyrimidinyl]-p-(methylthio)benzenesulfonamide, melting point 134°-136° C.

The starting material was prepared from 4,6-dichloro-5-(o-methoxybenzyl)pyrimidine and (p-methylthio)benzene-sulfonamide potassium. Melting point 157°-159° C.

EXAMPLE 62

In analogy to Example 59, from N-[6-chloro-5-(o-methoxybenzyl)-4-pyrimidinyl]-α,α,α-trifluoro-p-toluenesulfonamide, there was obtained N-[6-(2-hydroxyethoxy)-5-(o-methoxy-benzyl)-4-pyrimidinyl]-α,α,α-trifluoro-p-toluenesulfonamide, melting point 133°-134° C.

The starting material was obtained from 4,6-dichloro-5-(o-methoxybenzyl)pyrimidine and p-trifluoromethyl-benzenesulfonamide potassium, melting point 163° C.

EXAMPLE 63

In analogy to Example 59, from N-[6-chloro-5-(o-methoxybenzyl)-4-pyrimidinyl]-p-isopropylbenzenesulfonamide, there was obtained N-[6-(2-hydroxyethoxy)-5-(o-methoxybenzyl)-4-pyrimidinyl[-p-isopropylbenzenesulfonamide, melting point 112°-113° C.

The sodium salt, melting point 225° C., was prepared using sodium methylate in methanol.

The starting material was prepared from 4,6-dichloro-5-(o-methoxybenzyl)pyrimidine and isopropylbenzenesulfonamide potassium, melting point 138°-139° C.

EXAMPLE 64

In analogy to Example 59, from p-t-butyl-N-[6-chloro-5-(o-methoxybenzyl)-4-pyrimidinyl]benzenesulfonamide, there was obtained p-t-butyl-N-[6-(2-hydroxyethoxy)-5-(o-methoxy-benzyl)-4-pyrimidinyl]benzenesulfonamide, melting point 138°-140° C. (from diisopropyl ether).

The starting material was prepared from 4,6-dichloro-5-(o-methoxybenzyl)pyrimidine and p-t-butylbenzenesulfonamide potassium, melting point 215°–216° C.

EXAMPLE 65

In analogy to Example 59, from N-[6-chloro-5-(o-chlorobenzyl)-4-pyrimidinyl]-p-isopropylbenzenesulfonamide, there was obtained N-[6-(2-hydroxyethoxy)-5-(o-chlorobenzyl)-4-pyrimidinyl]-p-isopropylbenzenesulfonamide.

The starting material was prepared from 4,6-dichloro-5-(o-chlorobenzyl)pyrimidine and p-isopropylbenzenesulfonamide potassium, melting point 166°–167° C.

EXAMPLE 66

In analogy to Example 59, from N-[6-chloro-5-(o-(methylthio)benzyl)-4-pyrimidinyl]-p-isopropylbenzenesulfonamide, there was obtained N-[6-(2-hydroxyethoxy)-5-(o-methylthio)-benzyl)-4-pyrimidinyl]-p-isopropylbenzene-sulfonamide.

The starting material was prepared as follows:

By reacting thiosalicylic acid with dimethyl sulfate in the presence of tetrabutylammonium bromide, there was obtained methyl 2-(methylthio)benzoate, melting point 64° C. Reduction with lithium aluminum hydride in dry tetrahydrofuran yielded 2-(methylthio)benzyl alcohol which was converted by reaction with SOCl$_2$ into 2-(methylthio)benzyl chloride, boiling point 90° C./0.3 Torr. Reaction of diethyl malonate with 2-(methylthio)benzyl chloride yielded diethyl 2-(methylthio)-benzyl-malonate, boiling point 130° C./0.05 Torr. Condensation with formamidine yielded 5-[o-(methylthio)-benzyl]-6-hydroxy-4(3H)-pyrimidinone which was converted into 4,6-dichloro-5-[o-(methylthio)benzyl]-pyrimidine, melting point 91° C. From 4,6-dichloro-5-(o-(methylthio)benzyl)pyrimidine and p-isopropylbenzenesulfonamide potassium, there was finally obtained N-[6-chloro-5-(o-(methylthio)benzyl)-4-pyrimidinyl]-p-isopropylbenzenesulfonamide, melting point 145°–146° C.

EXAMPLE 67

In analogy to Example 59, from N-[6-chloro-5-(o-chlorobenzyl)-4-pyrimidinyl]-p-isobutylbenzenesulfonamide, there was obtained N-[6-(2-hydroxyethoxy)-5-(o-chlorobenzyl)-4-pyrimidinyl]-p-isobutylbenzenesulfonamide, melting point 130°–131° C.

The starting material was prepared from 4,6-dichloro-5-(o-chlorobenzyl)pyrimidine and p-isobutylbenzenesulfonamide potassium, melting point 147°–149° C.

EXAMPLE 69

In analogy to Example 50, from N-[6-chloro-5-(o-chlorobenzyl)-4-pyrimidinyl]-p-cyclohexylbenzenesulfonamide, there was obtained N-[6-(2-hydroxyethoxy)-5-(o-chlorobenzyl)-4-pyrimidinyl]-p-cyclohexylbenzenesulfonamide, melting point 164°–165° C.

The starting material was prepared from 4,6-dichloro-5-(o-chlorobenzyl)pyrimidine and p-cyclohexylbenzenesulfonamide potassium, melting point 107°–108° C.

EXAMPLE 70

In analogy to Example 59, from N-[6-chloro-5-(o-chlorobenzyl)-4-pyrimidinyl]-p-isopentylbenzenesulfonamide, there was obtained N-[6-(2-hydroxyethoxy)-5-(o-chlorobenzyl)-4-pyrimidinyl]-p-isopentylbenzenesulfonamide, melting point 127°–128° C. (from diisopropyl ether).

The starting material was prepared from 4,6-dichloro-5-(o-chlorobenzyl)pyrimidine and p-isopentylbenzenesulfonamide potassium, melting point 139°–140° C.

EXAMPLE 71

In analogy to Example 59, from N-[6-chloro-5-(o-methoxybenzyl)-4-pyrimidinyl]-p-(isopropylthio)benzenesulfonamide, there was obtained N-[6-(2-hydroxyethoxy)-5-(o-methoxy-benzyl)-4-pyrimidinyl]-p-(isopropylthio)benzenesulfonamide, melting point 127°–128° C. (from diisopropyl ether).

The starting material was prepared from 4,6-dichloro-5-(o-methoxybenzyl)pyrimidine and p-(isopropylthio)benzenesulfonamide potassium.

EXAMPLE 72

In analogy to Example 1, from p-chloro-N-[6-chloro-5-(p-chlorophenyl)-2-methyl-4-pyrimidinyl]benzenesuphonamide and ethylene glycol Na, there was obtained p-chloro-N-[5-(p-chlorophenyl)-6-(2-hydroxyethoxy)-2-methyl-4-pyrimidinyl]benzenesulfonamide, melting point 163°–164° C. (from ether).

The starting material was prepared as follows:

From diethyl p-chlorophenylmalonate, acetamidine hydrochloride and sodium methylate, there was prepared 5-(p-chlorophenyl)-2-methyl-4,6(1H,5H)-pyrimidinedione, melting point >270° C., and therefrom with POCl$_3$, there was prepared 4,6-dichloro-5-(p-chlorophenyl)-2-methylpyrimidine, melting point 181°–183° C. (from methylene chloride and isopropyl ether).

Reaction of this compound with p-chlorophenylsulfonamide yielded p-chloro-N-[6-chloro-5-(p-chlorophenyl)-2-methyl-4-pyrimidinyl]benzenesulfonamide, melting point 196°–197° C. (from acetonitrile).

EXAMPLE 73

In analogy to Example 1, from p-chloro-N-[6-chloro-5-(p-nitrophenyl)-4-pyrimidinyl]benzenesulfonamide and p-chlorophenylsulfonamide, there was obtained p-chloro-N-[6-(2-hydroxyethoxy)-5-(p-nitrophenyl)-4-pyrimidinyl]benzenesulfonamide, melting point 223°–225° C. (from methylene chloride and isopropyl ether).

The starting material was prepared as follows:

3.5 g of diethyl p-nitrophenylmalonate and 1.6 g of formamidine acetate were heated at 100° C. for 3 hours. Thereafter, an additional 3.2 g of formamidine acetate, 5 ml of absolute dimethylformamide and 1 ml of glacial acetic acid were added and the reaction mixture was heated at 110° C. for 16 hours. After evaporation of the solvent under reduced pressure, the residue was triturated with ether, filtered under suction and taken up in a 1N NaOH solution. The solution was treated with some charcoal, filtered and adjusted to pH=4.5 with glacial acetic acid. The precipitate was dried at 80° C. under reduced pressure. Thereafter, it was taken up in 20 ml of POCl$_3$ and 1 ml of dimethylaniline and boiled at reflux while stirring. After evaporation of the solvent under reduced pressure, the residue was taken up in ethyl acetate. The organic solution was washed with cold water, dried and evaporated. The residue was chromatographed on silica gel with cyclohexane-ether 9:1 and yielded 4,6-dichloro-5-(p-nitrophenyl)pyrimidine, melting point 159°–161° C. (from isopropyl ether).

Reaction of this compound with p-chlorophenylsulfonamide yielded p-chloro-N-[6-chloro-5-(p-nitrophenyl)-4-pyrimidinyl]benzenesulfonamide, melting point 282°-285° C. (from acetonitrile).

EXAMPLE 74

200 mg of p-chloro-N-[6-(2-hydroxyethoxy)-5-(p-nitrophenyl)-4-pyrimidinyl]benzenesulfonamide in 15 ml of glacial acetic acid and 2 ml of 4N HCl in dioxane were hydrogenated over 50 mg of palladium-carbon (10%) at room temperature and normal pressure. After filtering the catalyst under suction, the solution was evaporated under reduced pressure. The residue was dissolved in 30 ml of methanol and the solution was treated with 1 ml of dioxane-HCl. After 16 hours, the solution was evaporated under reduced pressure and the residue was recrystallized from methanol and acetonitrile. There was obtained N-[5-(p-aminophenyl)-6-(2-hydroxyethoxy)-4-pyrimidinyl]-p-chlorobenzenesulfonamide hydrochloride, melting point 206° C. (with decompositon).

EXAMPLE 75

In analogy to Example 1, from p-chloro-N-[5-(4-biphenylyl)-6-chloro-4-pyrimidinyl]benzenesulfonamide and ethylene glycol Na, there was obtained N-[5-(4-biphenylyl)-6-(2-hydroxyethoxy)-4-pyrimidinyl]-p-chlorobenzenesulfonamide, melting point 213°-214° C. (from ethyl acetate).

The starting material was prepared as follows:

From diethyl 4-biphenylmalonate, formamidine acetate and sodium methylate, there was obtained 5-(4-biphenylyl)-4,6(1H,5H)-pyrimidinedione, melting point >280° C. which, was reacted with POCl$_3$ to yield 5-(4-biphenylyl)-4,6-dichloropyrimidine, melting point 144° C. (from methylene chloride and n-hexane).

Reaction of this compound with p-chlorophenylsulfonamide yielded p-chloro-N-[5-(4-biphenylyl)-6-chloro-4-pyrimidinyl]benzenesulfonamide, melting point 234°-235° C. (from acetonitrile).

EXAMPLE 76

In analogy to Example 1, from p-chloro-N-(6-chloro-5-($\alpha,\alpha,\alpha$-trifluoro-p-tolyl)-4-pyrimidinyl]benzenesulfonamide and ethylene glycol Na, there was obtained p-chloro-N-[(6-hydroxy-ethoxy)-5-($\alpha,\alpha,\alpha$-trifluoro-p-tolyl)-4-pyrimidinyl]benzene-sulfonamide, melting point 171°-174° C. (from acetone and isopropyl ether).

The starting material was prepared as follows:

From $\alpha,\alpha,\alpha$-trifluoro-p-tolyl malonate and formamidine acetate, there was obtained 5-$\alpha,\alpha,\alpha$-trifluoro-p-tolyl)-4,6(1H,5H)-pyrimidinedione, melting point >280° C., which was reacted with POCl$_3$ to yield 4,6-dichloro-5-($\alpha,\alpha,\alpha$-p-tolyl)-pyrimidine, melting point 94°-95° C. (from n-hexane).

Reaction of this compound with p-chlorophenylsulfonamide yielded p-chloro-N-(6-chloro-5-($\alpha,\alpha,\alpha$-trifluoro-p-tolyl)-4-pyrimidinyl]benzenesulfonamide, melting point 262°-264° C. (from acetonitrile).

EXAMPLE 77

In analogy to Example 27, from N-[5-[p-(benzyloxy)-phenyl]-6-(2-hydroxyethoxy)-4-pyrimidinyl]-p-chlorobenzenesulfon-amide, there was obtained p-chloro-N-[5-(p-hydroxy-phenyl)-6-(2-hydroxyethoxy)-4-pyrimidinyl]benzenesulfonamide, melting point 207°-209° C. (from acetonitrile and isopropyl ether).

EXAMPLE 78

In analogy to Example 1, from N-[5-[p-(benzyloxy)-phenyl]-6-chloro-4-pyrimidinyl]-p-chlorobenzenesulfonamide and ethylene glycol Na, there was obtained N-[5-[p-(benzyloxy)phenyl]-6-(2-hydroxyethoxy)-4-pyrimidinyl]-p-chlorobenzenesulfonamide, melting point 160°-161° C. (from ether).

The starting material was prepared as follows:

From diethyl [p-(benzyloxy)phenyl]malonate and form-amidine acetate, there was obtained 5-[p-(benzyloxy)phenyl]-4,6(1H,5H)-dione, >280° C., which was reacted with POCl$_3$ to yield 5-[p-(benzyloxy)-phenyl]-4,6-dichloropyrimidine, melting point 115°-116° C. (from methylene chloride and isopropyl ether). Reaction of this compound with p-chlorophenylsulfonamide yielded N-[5-[p-(benzyloxy)-phenyl]-6-chloro-4-pyrimidinyl]-p-chlorobenzenesulfonamide, melting point 234°-236° C. (from ethyl acetate).

EXAMPLE 79

In analogy to Example 1, from N-[6-chloro-4-($\alpha,\alpha,\alpha$-trifluoro-p-tolyl)-4-pyrimidinyl]-$\alpha,\alpha,\alpha$-trifluoro-p-toluene-sulfonamide and ethylene glycol Na, there was obtained N-[6-(2-hydroxyethoxy)-5-($\alpha,\alpha,\alpha$-trifluoro-p-tolyl)-4-pyrimidinyl]-$\alpha,\alpha,\alpha$-trifluoro-p-toluenesulfonamide, melting point 165°-166° C. (from methylene chloride and isopropyl ether).

The starting material was prepared from 4,6-dichloro-5-$\alpha,\alpha,\alpha$-p-tolyl)-pyrimidine and $\alpha,\alpha,\alpha$-trifluoro-p-tolylsulfonamide, melting point >270° C. (from acetonitrile).

EXAMPLE 80

In analogy to Example 1, from p-chloro-N-[6-chloro-5-(2-naphthylmethyl)-4-pyrimidinyl]benzenesulfonamide and ethylene glycol Na, there was obtained p-chloro-N-[6-(2-hydroxyethoxy)-5-(2-naphthylmethyl)-4-pyrimidinyl]benzenesulfonamide, melting point 161° C. (from acetonitrile and isopropyl ether).

The starting material was prepared as follows:

From diethyl (2-naphthylmethyl)malonate and form-amidine acetate there was obtained 5-(2-naphthylmethyl)-4,6(1H,5H)-pyrimidinedione, melting point >270° C., and which was reacted with POCl$_3$ to yield 4,6-dichloro-5-(2-naphthylmethyl)-pyrimidine, melting point 161°-162° C. (from methylene chloride and isopropyl ether).

Reaction of this compound with p-chlorophenylsulfonamide yielded p-chloro-N-[6-chloro-5-(2-naphthylmethyl)-4-pyrimidinyl]benzenesulfonamide, melting point 197°-199° C. (from acetonitrile).

EXAMPLE 81

In analogy to Example 1, from N-[5-(p-bromophenyl)-6-chloro-4-pyrimidinyl]-p-isopropylbenzenesulfonamide and ethylene glycol Na, there was obtained N-[5-(p-bromophenyl)-6-(2-hydroxyethoxy)-4-pyrimidinyl]-p-isopropylbenzene-sulfonamide, melting point 207°-208° C. (from acetonitrile and isopropyl ether).

The starting material was prepared from 5-(p-bromophenyl)-4,6-dichloropyrimidine and p-isopropylbenzene-sulfonamide, melting point 271°-273° C. (from acetonitrile).

EXAMPLE 82

In analogy to Example 1, from N-[6-chloro-5-(p-chlorophenyl)-4-pyrimidinyl]-p-isopropylbenzenesulfonamide and ethylene glycol Na, there was obtained N-[5-(p-chlorophenyl)-6-(2-hydroxyethoxy)-4-pyrimidinyl]-p-isopropylbenzenesulfonamide, melting point 162°-164° C. (from acetonitrile and isopropyl ether).

The starting material was prepared from 4,6-dichloro-5-(p-chlorophenyl)pyrimidine and p-isopropylbenzenesulfonamide, melting point 266°-268° C. (from acetonitrile).

EXAMPLE 83

In analogy to Example 1, from N-(6-chloro-5-p-tolyl-4-pyrimidinyl)-p-isopropylbenzenesulfonamide and ethylene glycol Na, there was obtained N-[6-hydroxyethoxy)-5-p-tolyl-4-pyrimidinyl]-p-isopropylbenzenesulfonamide, melting point 142°-144° C. (from isopropyl ether).

With sodium methylate there was obtained therefrom the Na salt, as an amorphous substance.

The starting material, N-(6-chloro-5-p-tolyl-4-pyrimidinyl)-p-isopropylbenzenesulfonamide, melting point 211°-213° C. (from acetonitrile), was prepared from 4,6-dichloro-5-p-tolylpyrimidine and p-isopropylbenzenesulfonamide.

EXAMPLE 84

In analogy to Example 1, from p-tert-butyl-N-(6-chloro-5-p-tolyl-4-pyrimidinyl)benzenesulfonamide and ethylene glycol Na, there was obtained p-tert-butyl-N-[6-(2-hydroxyethoxy)-5-p-tolyl-4-pyrimidinyl]benzenesulfonamide, melting point 169°-170° C. (from isopropyl ether), which was reacted with sodium methylate to yield the amorphous Na salt.

The starting material was prepared from 4,6-dichloro-5-p-tolylpyrimidine and p-tert-butylbenzenesulfonamide, melting point 222°-224° C. (from acetonitrile).

EXAMPLE 85

In analogy to Example 1, from N-(6-chloro-5-p-tolyl-4-pyrimidinyl)-p-(2-methoxyethoxy)benzenesulfonamide and ethylene glycol Na, there was obtained N-[6-(2-hydroxyethoxy)-5-p-tolyl-4-pyrimidinyl]-p-(2-methoxyethoxy)benzenesulfon-amide, melting point 155°-156° C. (from isopropyl ether).

The starting material was prepared from 4,6-dichloro-5-p-tolylpyrimidine and p-(2-methoxyethoxy)benzenesulfonamide, melting point 172°-173° C. (from methylene chloride and isopropyl ether).

EXAMPLE 86

In analogy to Example 1, from N-(6-chloro-5-p-tolyl-4-pyrimidinyl)-p-(trifluoromethoxy)benzenesulfonamide and ethylene glycol Na, there was obtained N-[6-(2-hydroxyethoxy)-5-p-tolyl-4-pyrimidinyl]-p-(trifluoromethoxy)benzenesulfonamide, melting point 147°-148° C. (from isopropyl ether).

The starting material was prepared from 4,6-dichloro-5-p-tolylpyrimidine and p-(trifluoromethoxy)benzenesulfonamide, melting point 205°-206° C. (from acetonitrile and isopropyl ether).

EXAMPLE 87

In analogy to Example 1, from p-butyl-N-(6-chloro-5-p-tolyl-4-pyrimidinyl)benzenesulfonamide and ethylene glycol Na, there was obtained p-butyl-N-[6-(2-hydroxyethoxy)-5-p-tolyl-4-pyrimidinyl]benzenesulfonamide, melting point 136°-137° C. (from isopropyl ether).

The starting material was prepared from 4,6-dichloro-5-p-tolylpyrimidine and p-butylbenzenesulfonamide, melting point 168°-169° C. (from acetonitrile and isopropyl ether).

EXAMPLE 88

In analogy to Example 1, from N-(6-chloro-5-p-tolyl-4-pyrimidinyl)-2-naphthalenesulfonamide and ethylene glycol Na, there was obtained N-[6-(2-hydroxyethoxy)-5-p-tolyl-4-pyrimidinyl]-2-naphthalenesulfonamide, melting point 161°-162° C. (from acetone and isopropyl ether).

The starting material was prepared from 4,6-dichloro-5-p-tolylpyrimidine and 2-naphthalenesulfonamide, melting point 198°-202° C. (from acetonitrile).

EXAMPLE 89

In analogy to Example 1, from N-(6-chloro-5-p-tolyl-4-pyrimidinyl)-p-toluenesulfonamide and ethylene glycol Na, there was obtained N-[6-(2-hydroxyethoxy)-5-p-tolyl-4-pyrimidinyl]-p-toluenesulfonamide, melting point 169°-170° C. (from acetone and isopropyl ether).

The starting material was prepared from 4,6-dichloro-5-p-tolylpyrimidine and p-toluenesulfonamide, melting point 213°-214° C. (from acetonitrile and isopropyl ether).

EXAMPLE 90

In analogy to Example 1, from N-(6-chloro-5-p-tolyl-4-pyrimidinyl)-α,α,α-trifluoro-p-toluenesulfonamide and ethylene glycol Na, there was obtained N-[6-(2-hydroxyethoxy)-5-p-tolyl-4-pyrimidinyl]-α,α,α-trifluoro-p-toluenesulfonamide, melting point 162°-163° C. (from acetonitrile and isopropyl ether).

The starting material was prepared from 4,6-dichloro-5-p-tolylpyrimidine and α,α,α-trifluoro-p-toluenesulfonamide, melting point 231°-233° C. (from acetonitrile).

EXAMPLE 91

In analogy to Example 1, from N-(6-chloro-5-p-tolyl-4-pyrimidinyl)-p-fluorobenzenesulfonamide and ethylene glycol Na, there were obtained, after chromatography, p-fluoro-N-[6-(2-hydroxyethoxy)-5-p-tolyl-4-pyrimidinyl]benzenesulfonamide, melting point 167°-168° C. (from acetone and isopropyl ether), and p-(2-hydroxyethoxy)-N-[6-(2-hydroxyethoxy)-5-p-tolyl-4-pyrimidinyl]benzenesulfonamide, melting point 174°-176° C. (from acetone and isopropyl ether).

The starting material was prepared from 4,6-dichloro-5-p-tolylpyrimidine and p-fluorobenzenesulfonamide, melting point 207°-208° C. (from acetonitrile and isopropyl ether).

EXAMPLE 92

In analogy to Example 1, from N-(6-chloro-5-p-tolyl-4-pyrimidinyl)-p-propylbenzenesulfonamide and ethylene glycol Na, there was obtained N-[6-(2-hydroxyethoxy)-5-p-tolyl-4-pyrimidinyl]-p-propylbenzenesulfonamide, melting point 152°-153° C. (from isopropyl ether).

EXAMPLE 93

In analogy to Example 1, from N-(6-chloro-5-p-tolyl-4-pyrimidinyl)-o-propylbenzenesulfonamide and ethylene glycol Na, there was obtained N-[6-(2-hydroxyethoxy)-5-p-tolyl-4-pyrimidinyl]-o-propylbenzenesulfonamide, melting point 195°-196° C. (from methylene chloride and isopropyl ether).

The starting material was prepared from 4,6-dichloro-5-p-tolylpyrimidine and o-propylbenzenesulfonamide, melting point 150°-151° C. (from isopropyl ether).

EXAMPLE 94

In analogy to Example 1, from N-(6-chloro-5-p-tolyl-4-pyrimidinyl)-p-ethylbenzenesulfonamide and ethylene glycol Na, there was obtained p-ethyl-N-[6-(2-hydroxyethoxy)-5-p-tolyl-4-pyrimidinyl]benzenesulfonamide, melting point 138°-139° C. (from methylene chloride and isopropyl ether).

The starting material was prepared from 4,6-dichloro-5-p-tolypyrimidine and p-ethylbenzenesulfonamide, melting point 180°-181° C. (from acetonitrile).

EXAMPLE 95

In analogy to Example 1, from N-(6-chloro-5-p-tolyl-4-pyrimidinyl)-o-ethylbenzenesulfonamide and ethylene glycol Na, there was obtained o-ethyl-N-[6-(2-hydroxyethoxy)-5-p-tolyl-4-pyrimidinyl]benzenesulfonamide, melting point 136°-138° C. (from acetone and isopropyl ether).

The starting material was prepared from 4,6-dichloro-5-p-tolylpyrimidine and o-ethylbenzenesulfonamide, melting point 159°-160° C. (from acetonitrile and isopropyl ether).

EXAMPLE 96

In analogy to Example 1, from N-(6-chloro-5-p-tolyl-4-pyrimidinyl)-p-cyclopentylbenzenesulfonamide and ethylene glycol Na, there was obtained p-cyclopentyl-N-[6-(2-hydroxy-ethoxy)-5-p-tolyl]benzenesulfonamide, melting point 179°-181° C. (from acetone and isopropyl ether).

The starting material was prepared from 4,6-dichloro-5-p-tolylpyrimidine and p-cyclopentylbenzenesulfonamide, melting point 192°-194° C. (from acetonitrile and isopropyl ether).

EXAMPLE 97

In analogy to Example 1, from N-(6-chloro-5-p-tolyl-4-pyrimidinyl)-α,α,α-trifluoro-o-toluenesulfonamide and ethylene glycol Na, there was obtained α,α,α-trifluoro-N-[6-(2-hydroxyethoxy)-5-p-tolyl-4-pyrimidinyl]-o-toluenesulfonamide, melting point 166°-167° C. (from methylene chloride and isopropyl ether).

The starting material was prepared from 4,6-dichloro-5-p-tolylpyrimidine and α,α,α-trifluoro-o-toluenesulfonamide, melting point 129°-131° C. (from methylene chloride and isopropyl ether).

EXAMPLE 98

In analogy to Example 1, from N-(6-chloro-5-p-tolyl-4-pyrimidinyl)-o-toluenesulfonamide and ethylene glycol Na, there was obtained N-[6-(2-hydroxyethoxy)-5-p-tolyl-4-pyrimidinyl]-o-toluenesulfonamide, melting point 149°-150° C. (from ethyl acetate and isopropyl ether).

The starting material was prepared from 4,6-dichloro-5-p-tolylpyrimidine and o-toluenesulfonamide, melting point 198°-199° C. (from acetonitrile).

EXAMPLE 99

In analogy to Example 1, from N-(6-chloro-5-p-tolyl-4-pyrimidinyl)-2,4-xylenesulfonamide and ethylene glycol Na, there was obtained N-[6-(2-hydroxyethoxy)-5-p-tolyl-4-pyrimidinyl]-2,4-xylenesulfonamide, melting point 158°-159° C. (from isopropyl ether).

The starting material was prepared from 4,6-dichloro-5-p-tolylpyrimidine and 2,4-xylenesulfonamide, melting point 233° C. (from acetonitrile and isopropyl ether).

EXAMPLE 100

In analogy to Example 1, from p-chloro-N-[6-chloro-5-(1-naphthylmethyl)-4-pyrimidinyl]benzenesulfonamide and ethylene glycol Na, there was obtained p-chloro-N-[6-(2-hydroxyethoxy)-5-(1-naphthylmethyl)-4-pyrimidinyl]benzenesulfonamide, melting point 204°-205° C. (from acetonitrile and isopropyl ether).

The starting material was prepared as follows:

From diethyl 1-naphthylmalonate and formamidine acetate, there was obtained 5-(1-naphthylmethyl)-4,6(1H,5H)-pyrimidinedione, melting point >270° C., which, after drying under reduced pressure at 80° C., was reacted with POCl$_3$ to yield 4,6-dichloro-5-(1-naphthylmethyl)-pyrimidine, melting point 111°-112° C. (from methylene chloride and isopropyl ether).

Reaction of this compound with p-chlorophenylsulfonamide yielded p-chloro-N-[6-chloro-5-(1-naphthylmethyl)-4-pyrimidinyl]benzenesulfonamide, melting point 202°-203° C. (from acetonitrile).

EXAMPLE 101

In analogy to Example 1, from N-[6-chloro-5-(p-isopropylphenyl)-4-pyrimidinyl]-p-isopropylbenzenesulfonamide and ethylene glycol Na, there was obtained N-[6-(2-hydroxyethoxy)-5-(p-isopropylphenyl)-4-pyrimidinyl]-p-isopropylbenzenesulfon-amide, melting point 142°-144° C. (from isopropyl ether).

The starting material was prepared as follows:

From diethyl (p-isopropylphenyl)malonate and formamidine acetate, there was obtained 5-(p-isopropylphenyl)-4,6(1H,5H)-pyrimidinedione, melting point >290° C., which was reacted with POCl$_3$ to yield 4,6-dichloro-5-(p-isopropylphenyl)pyrimidine, melting point 69°-70° C. (from n-hexane). Reaction of this compound with p-isopropylbenzenesulfonamide yielded N-[6-chloro-5-(p-isopropylphenyl)-4-pyrimidinyl]-p-isopropylbenzenesulfonamide, melting point 198°-199° C. (from acetonitrile and isopropyl ether).

EXAMPLE 102

In analogy to Example 1, from N-[6-chloro-5-(p-isopropylphenyl)-4-pyrimidinyl]-p-cyclopentylbenzenesulfonamide and ethylene glycol Na, there was obtained p-cyclopentyl-N-[6-(2-hydroxyethoxy)-5-(p-isopropylphenyl)-4-pyrimidinyl]benzenesulfonamide, melting point 132° C. (decomposition) (from acetoneisopropyl ether).

The starting material was prepared from 4,6-dichloro-5-(p-isopropylphenyl)pyrimidine and p-cyclopentylbenzenesulfon-amide, melting point 188°–189° C. (from methylene chloride and isopropyl ether).

EXAMPLE 103

By heating of p-t-butyl-N-[6-chloro-5-(o-methoxybenzyl)-4-pyrimidinyl]benzenesulphonamide and pyridine-2-carboxylic acid in methylene chloride in the presence of dicyclohexylcarbodiimide there was obtained 4-t-butyl-N-[6-[2-(pyridin-2-yl-carbonyloxy)ethoxy]-5-(2-methoxybenzyl)pyrimidin-4-yl]benzenesulphonamide.

In analogous manner there were obtained 4-t-butyl-N-[6-[2-(pyridin-3-ylcarbonyloxy)ethoxy]-5-(2-methoxybenzyl)pyrimidin-4-yl]benzenesulphonamide;

4-t-butyl-N-[6-[2-(pyridin-4-ylcarbonyloxy)ethoxy-5-(2-methoxybenzyl)pyrimidin-4-yl]benzenesulphonamide;

4-t-butyl-N-[6-[2-[(3-methylisoxazol-5-yl)carbonyloxy]-ethoxy-5-(2-methoxybenzyl)pyrimidin-4-yl]benzenesulphonamide;

4-t-butyl-N-[6-[2-(furan-2-ylcarbonyloxy)ethoxy]-5-(2-methoxybenzyl)pyrimidin-4-yl]benzenesulphonamide;

4-t-butyl-N-[6-[2-(furan-3-ylcarbonyloxy)ethoxy]-5-(2-methoxybenzyl)pyrimidin-4-yl]benzenesulphonamide;

4-t-butyl-N-[6-[2-(thiophen-2-ylcarbonyl)ethoxy]-5-(2-methoxybenzyl)pyrimidin-4-yl]benzenesulphonamide;

4-t-butyl-N-[6-[2-(thiophen-3-ylcarbonyl)ethoxy]-5-(2-methoxybenzyl)pyrimidin-4-yl]benzenesulphonamide.

EXAMPLE 104

From diethyl p- tolylmalonate and 2-pyrimidine carboximide amide there was obtained
(R,S)-5-(4-methyl-phenyl)-2-(pyrimidin-2-yl)-1,4,5,6-tetrahydropyrimidine-4,6-dione
that was converted into
4,6-dichloro-5-(4-methyl-phenyl)-2,2'-bipyrimidinyl
by treatment with POCl$_3$. Reaction of the dichloro compound with potassium 4-t-butylphenyl sulfonamide afforded potassium
4-tert-butyl-N-[6-chloro-5-(4-methyl-phenyl)-2,2'-bipyrimidine-4-yl]benzenesulfonamide
that was converted by reaction with sodium glycolate into
4-tert.-butyl-N-[6-(2-hydroxy-ethoxy)-5-(4-methyl-phenyl)-2,2'-bipyrimidin-4-yl]benzenesulfonamide.

EXAMPLE A

Tablets containing the following ingredients can be produced in a conventional manner:

| Ingredients | Per tablet |
|---|---|
| A Compound of formula I | 10.0–100.0 mg |
| Lactose | 125.0 mg |
| Corn starch | 75.0 mg |
| Talc | 4.0 mg |
| Magnesium stearate | 1.0 mg |

EXAMPLE B

Capsules containing the following ingredients can be produced in a conventional manner:

| Ingredients | Per tablet |
|---|---|
| A compound of formula I | 25.0 mg |
| Lactose | 150.0 mg |
| Corn starch | 20.0 mg |
| Talc | 5.0 mg |

EXAMPLE C

Injection solutions can have the following composition:

| | |
|---|---|
| A Compound of formula I | 3.0 mg |
| Gelatin | 150.0 mg |
| Phenol | 4.7 mg |
| Water for injection solutions ad | 1.0 mg |

EXAMPLE D 500 mg of a compound of formula I are suspended in 3.5 ml of Myglyol 812 and 0.08 g of benzyl alcohol. This suspension is filled into a container having a dosage valve. 5.0 g of Freon 12 are charged into the container through the valve. The Freon is dissolved in the Myglyol-benzyl alcohol mixture by shaking. This spray container contains about 100 single doses which can be administered individually.

We claim:

1. A method of treating circulatory disorders which comprises administering an effective amount of a compound of the formula $$\begin{array}{c} R^2 \quad R^1 \qquad R^6 \quad X(CH_2)_nYR^5 \\ \diagup \!\!\!\! \diagdown \!\!\!\! - SO_2NH - \!\!\!\! \diagup \!\!\!\! \diagdown \!\!\!\! N \\ R^3 \qquad \qquad N \!\!\!\! - \!\!\!\! \diagdown \!\!\!\! R_4 \end{array} \quad I$$

wherein $R^1$ is hydrogen, lower-alkyl, lower alkoxy, lower-alkylthio, halogen or trifluoromethyl;

$R^2$ is hydrogen, halogen, lower-alkoxy, hydroxy-lower-alkoxy or trifluoromethyl; and $R^3$ is hydrogen, hydroxy, halogen, alkylthio, cycloalkyl, lower-alkyl, hydroxy-lower-alkyl, hydroxy-lower-alkoxy, hydroximino-lower-alkyl, lower-alkenyl, oxo-lower-alkyl, trifluoromethyl, trifluoromethoxy, lower-alkoxy, lower-alkoxy-lower-alkoxy or aryl-lower-alkoxy wherein aryl is phenyl or phenyl substituted with at least one of halogen, lower-alkyl or lower-alkoxyl or $R^2$ and $R^3$ taken together are butadienyl;

$R^4$ is hydrogen, lower-alkyl, phenyl, phenyl substituted with at least one of halogen, lower-alkyl or lower alkoxy, or a monocyclic five or six membered aromatic ring having at least one nitrogen or sulfur atom selected from the group consisting of pyrimidinyl, pyridyl, pyrazinyl, pyridazinyl and thienyl;

$R^5$ is hydrogen, lower-alkanoyl, benzoyl, heterocyclylcarbonyl selected from the group consisting of 2-pyridylcarbonyl, 3-pyridylcarbonyl, 4-pyridylcarbonyl, 3-methylisoxazol-5-yl-carbonyl, 2-furoyl, 3-furoyl, 2-thenoyl and 3-thenoyl or tetrahydropyran-2-yl;

$R^6$ is a residue of the formula

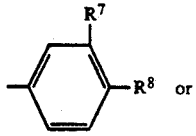 (a)

or

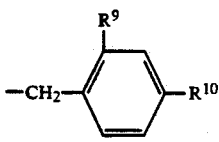 (b)

$R^7$ is hydrogen, lower-alkoxy or nitro; and $R^8$ is hydrogen, halogen, lower-alkyl, lower-alkoxy, lower-alkylthio, nitro, hydroxy, amino or trifluoromethyl; or $R^7$ and $R^8$ taken together are butadienyl;

$R^9$ is hydrogen, halogen, lower-alkyl, lower-alkoxy, lower-alkylthio or trifluoromethyl;

$R^{10}$ is hydrogen, halogen, lower-alkyl, lower-alkoxy or lower-alkylthio;

X and Y each, independently, is O, S or NH; and n is 2, 3 or 4;

or a pharmaceutical acceptable salt thereof.

2. A method according to claim 1, wherein $R^4$ is hydrogen, lower-alkyl, phenyl or phenyl substituted with at least one of halogen, lower-alkyl or lower-alkoxy.

3. A compound of formula

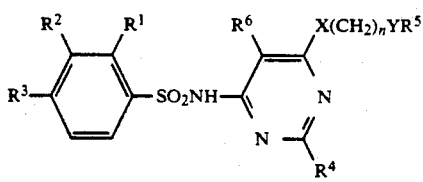

$R^1$ is hydrogen, lower-alkyl, lower-lkoxy, lower-alkylthio, halogen or trifluoromethyl;

$R^2$ is hydrogen, halogen, lower-alkoxy, hydroxy-lower-alkoxy or trifluoromethyl; and $R^3$ is hydrogen, hydroxy, halogen, alkylthio, cycloalkyl, lower-alkyl, hydroxy-lower-alkyl, hydroxy-lower-alkoxy, hydroximino-lower-alkyl, lower-alkenyl, oxo-lower-alkyl, trifluoromethyl, trifluoromethoxy, lower-alkoxy, lower-alkoxy-lower-alkoxy or aryl-lower-alkoxy wherein aryl is phenyl or phenyl substituted with at least one of halogen, lower-alkyl or lower-alkoxy; or $R^2$ and $R^3$ taken together are butadienyl;

$R^4$ is hydrogen, lower-alkyl, phenyl, phenyl substituted with at least one of halogen, lower-alkyl or lower alkoxy, or a monocyclic five or six membered aromatic ring having at least one nitrogen or sulfur atom selected from the group consisting of pyrimidinyl, pyridyl, pyrazinyl, pyridazinyl and thienyl;

$R^5$ is hydrogen, lower-alkanoyl, benzoyl, heterocyclylcarbonyl selected from the group consisting of 2-pyridylcarbonyl, 3-pyridylcarbonyl, 4-pyridylcarbonyl, 3-methylisoxazol-5-yl-carbonyl, 2-furoyl, 3-furoyl, 2-thenoyl and 3-thenoyl or tetrahydropyran-2-yl;

$R^6$ is a residue of the formula

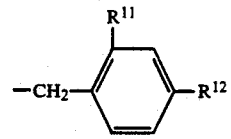 (c)

$R^{11}$ is halogen, lower-alkoxy, lower-alkylthio or trifluoromethyl;

$R^{12}$ is hydrogen or lower-alkoxy;

X and Y each, independently, is O, S, or NH; and n is 2, 3 or 4;

or a pharmaceutically acceptable salt thereof.

4. A compound according to claim 3, wherein $R^4$ is hydrogen, lower-alkyl, phenyl or phenyl substituted with at least one of halogen, lower-alkyl or lower-alkoxy.

5. A compound according to claim 3 wherein the compound is N-[6-(2-hydroxyethoxy)-5-(o-methoxybenzyl)-4-pyrimidinyl]-p-isopropylbenzenesulfonamide.

6. A compound according to claim 3 wherein the compound is p-t-butyl-N-[6-(2-hydroxyethoxy)-5-(o-methoxybenzyl)-4-pyrimidinyl]benzenesulfonamide.

7. A compound according to claim 3 wherein the compound is N-[6-(2-hydroxyethoxy)-5-(o-chlorobenzyl)-4-pyrimidinyl]-p-isopropylbenzenesulfonamide.

8. A compound according to claim 3 wherein the compound is N-[6-(2-hydroxyethoxy)-5-(o-methylthiobenzyl)-4-pyrimidinyl]-p-isopropylbenzenesulfonamide.

9. A compound of the formula

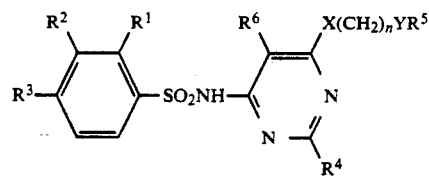

wherein $R^1$ is hydrogen, lower-alkyl, lower alkoxy, lower-alkylthio, halogen or trifluoromethyl;

$R^2$ is hydrogen, halogen, lower-alkoxy, hydroxy-lower-alkoxy or trifluoromethyl; and $R^3$ is hydrogen, hydroxy, halogen, alkylthio, cycloalkyl, lower-alkyl, hydroxy-lower-alkyl, hydroxy-lower-alkoxy, hydroximino-lower-alkyl, lower-alkenyl, oxo-lower-alkyl, trifluoromethyl, trifluoromethoxy, lower-alkoxy, lower-alkoxy-lower-alkoxy or aryl-lower-alkoxy, wherein aryl is phenyl or phenyl substituted with at least one of halogen, lower-alkyl or lower-alkoxy; or $R^2$ and $R^3$ taken together are butadienyl;

$R^4$ is hydrogen, lower-alkyl, phenyl, phenyl substituted with at least one of halogen, lower-alkyl or lower alkoxy, or a monocyclic five or six membered aromatic ring having at least one nitrogen or sulfur atom selected from the group consisting of pyrimidinyl, pyridyl, pyrazinyl, pyridazinyl and thienyl;

$R^5$ is hydrogen, lower-alkanoyl, benzoyl, heterocyclylcarbonyl selected from the group consisting of 2-pyridylcarbonyl, 3-pyridylcarbonyl, 4-pyridylcarbonyl, 3-methylisoxazol-5-yl-carbonyl, 2-furoyl, 3-furoyl, 2-thenoyl and 3-thenoyl or tetrahydropyran-2-yl;

$R^6$ is a residue of the formula

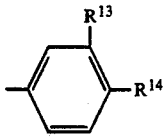 (d)

$R^{13}$ is hydrogen, lower-alkoxy or nitro;

$R^{14}$ is hydrogen, halogen, lower-alkyl, lower-alkoxy, lower-alkylthio or nitro; or $R^{13}$ and $R^{14}$ taken together are butadienyl;

X and Y each, independently, is O, S, or NH; and n is 2, 3 or 4;

or a pharmaceutically acceptable salt thereof.

10. A compound according to claim 9, wherein $R^4$ is hydrogen, lower-alkyl, phenyl or phenyl substituted with at least one of halogen, lower-alkyl or lower-alkoxy.

11. A compound according to claim 9 wherein the compound is N-[5-(p-chlorophenyl)-6-(2-hydroxyethoxy)-4-pyrimidinyl]-α,α,α-trifluoro-p-toluenesulfonamide.

12. A compound according to claim 9 wherein the compound is N-[5-(p-chlorophenyl)-6-(2-hydroxyethoxy)-4-pyrimidinyl]-p-isopropylbenzenesulfonamide.

13. A compound according to claim 9 wherein the compound is N-[5-(p-bromophenyl)-6-(2-hydroxyethoxy)-4-pyrimidinyl]-p-isopropylbenzenesulfonamide.

14. A compound according to claim 9 wherein the compound is N-[6-(2-hydroxyethoxy)-5-(α,α,α-trifluoro-p-tolyl)-4-pyrimidinyl]-α,α,α-trifluoro-p-toluenesulfonamide.

15. A compound according to claim 9 wherein the compound is N-[6-hydroxyethoxy)-5-p-tolyl-4-pyrimidinyl]-p-isopropylbenzenesulfonamide.

16. A compound according to claim 9 wherein the compound is N-[6-(2-hydroxyethoxy)-5-(α,α,α-trifluoro-p-tolyl)-4-pyrimidinyl]-p-isopropylbenzenesulfonamide.

17. A compound according to claim 9 wherein the compound is p-tert-butyl-N-[6-(2-hydroxyethoxy)-5-p-tolyl-4-pyrimidinyl]benzenesulfonamide.

18. A compound according to claim 9 wherein the compound is p-ethyl-N-[6-(2-hydroxyethoxy)-5-p-tolyl-4-pyrimidinyl]benzenesulfonamide.

19. A compound according to claim 9 wherein the compound is o-ethyl-N-[6-(2-hydroxyethoxy)-5-p-tolyl-4-pyrimidinyl]benzenesulfonamide.

20. A pharmaceutical composition comprising a compound of the formula

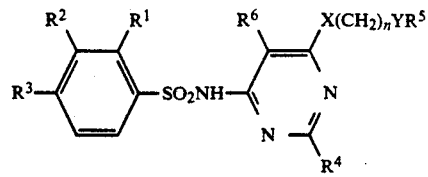

$R^1$ is hydrogen, lower-alkyl, lower alkoxy, lower-alkylthio, halogen or trifluoromethyl;

$R^2$ is hydrogen, halogen, lower-alkoxy, hydroxy-lower-alkoxy or trifluoromethyl; and $R^3$ is hydrogen, hydroxy, halogen, alkylthio, cycloalkyl, lower-alkyl, hydroxy-lower-alkyl, hydroxy-lower-alkoxy, hydroximino-lower-alkyl, lower-alkenyl, oxo-lower-alkyl, trifluoromethyl, trifluoromethoxy, lower-alkoxy, lower-alkoxy-lower-alkoxy or aryl-lower-alkoxy, wherein aryl is phenyl or phenyl substituted with at least one of halogen, lower-alkyl or lower-alkoxy; or $R^2$ and $R^3$ taken together are butadienyl;

$R^4$ is hydrogen, lower-alkyl, phenyl, phenyl substituted with at least one of halogen, lower-alkyl or lower alkoxy, or a monocyclic five or six membered aromatic ring having at least one nitrogen or sulfur atom selected from the group consisting of pyrimidinyl, pyridyl, pyrazinyl, pyridazinyl and thienyl;

$R^5$ is hydrogen, lower-alkanoyl, benzoyl, heterocyclylcarbonyl selected from the group consisting of 2-pyridylcarbonyl, 3-pyridylcarbonyl, 4-pyridylcarbonyl, 3-methylisoxazol-5-yl-carbonyl, 2-furoyl, 3-furoyl, 2-thenoyl and 3-thenoyl or tetrahydropyran-2-yl;

$R^6$ is a residue of the formula

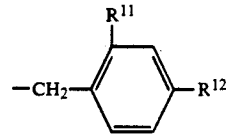 (c)

wherein $R^{11}$ is halogen, lower-alkoxy, lower-alkyl-thio or trifluoromethyl;

$R^{12}$ is hydrogen or lower-alkoxy;

X and Y each, independently, is O, S, or NH; and n is 2, 3 or 4;

or a pharmaceutically acceptable salt thereof and an inert carrier.

21. A pharmaceutical composition according to claim 20, wherein $R^4$ is hydrogen, lower-alkyl phenyl or phenyl substituted with at least one of halogen, lower-alkyl or lower-alkoxy.

22. A pharmaceutical composition comprising a compound of the formula

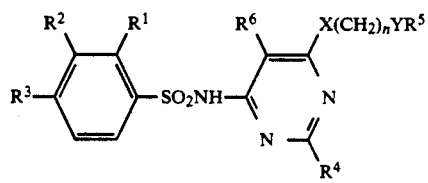

wherein $R^1$ is hydrogen, lower-alkyl, lower alkoxy, lower-alkylthio, halogen or trifluoromethyl;

$R^2$ is hydrogen, halogen, lower-alkoxy, hydroxy-lower-alkoxy or trifluoromethyl; and $R^3$ is hydrogen, hydroxy, halogen, alkylthio, cycloalkyl, lower-alkyl, hydroxy-lower-alkyl, hydroxy-lower-alkoxy, hydroximino-lower-alkyl, lower-alkenyl, oxo-lower-alkyl, trifluoromethyl, trifluoromethoxy, lower-alkoxy, lower-alkoxy-lower-alkoxy or aryl-lower-alkoxy, wherein aryl is phenyl or phenyl substituted with at least one of halogen, lower-alkyl or lower-alkoxy; or $R^2$ and $R^3$ taken together are butadienyl;

$R^4$ is hydrogen, lower-alkyl, phenyl, phenyl substituted with at least one of halogen, lower-alkyl or lower alkoxy, or a monocyclic five or six membered aromatic ring having at least one nitrogen or sulfur atom selected from the group consisting of pyrimidinyl, pyridyl, pyrazinyl, pyridazinyl and thienyl;

$R^5$ is hydrogen, lower-alkanoyl, benzoyl, heterocyclylcarbonyl selected from the group consisting of 2-pyridylcarbonyl, 3-pyridylcarbonyl, 4-pyridylcarbonyl, 3-methylisoxazol-5-yl-carbonyl, 2-furoyl, 3-furoyl, 2-thenoyl and 3-thenoyl or tetrahydropyran-2-yl;

$R^6$ is a residue of the formula

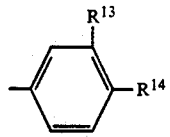

(d)

$R^{13}$ is hydrogen, lower-alkoxy or nitro;

$R^{14}$ is hydrogen, halogen, lower alkyl, lower-alkoxy, lower-alkylthio or nitro; or $R^{13}$ and $R^{14}$ taken together are butadienyl;

X and Y each, independently, is O, S or NH; and n is 2, 3 or 4;

or a pharmaceutically acceptable salt thereof, and an inert carrier.

23. A pharmaceutical composition according to claim 22, wherein $R^4$ is hydrogen, lower-alkyl, phenyl or phenyl substituted with at least one of halogen, lower-alkyl or lower-alkoxy.

24. A compound, according to claim 3, wherein the compound is

α,α,α-trifluoro-N-[6-(2-hydroxyethoxy)-6-[o-∂(trifuoromethyl)benzyl]pyrimidinyl]-p-toluenesulfonamide.

25. A compound, according to claim 9, wherein the compound is

N-[5-(p-chlorophenyl)-6-(2-hydroxyethoxy)-4-pyrimidinyl]-α,α,α-trifluoro-p-toluenesulfonamide.

* * * * *